US008318938B2

(12) United States Patent
Nichols et al.

(10) Patent No.: US 8,318,938 B2
(45) Date of Patent: Nov. 27, 2012

(54) TRANS-FUSED CHROMENOISOQUINOLINES SYNTHESIS AND METHODS FOR USE

(75) Inventors: David Nichols, West Lafayette, IN (US); Val J. Watts, West Lafayette, IN (US)

(73) Assignee: Purdue Research Foundation, West Lafayette, IN (US)

(*) Notice: Subject to any disclaimer, the term of this patent is extended or adjusted under 35 U.S.C. 154(b) by 1060 days.

(21) Appl. No.: 12/195,141

(22) Filed: Aug. 20, 2008

(65) Prior Publication Data

US 2009/0030025 A1 Jan. 29, 2009

Related U.S. Application Data

(63) Continuation of application No. PCT/US2007/062481, filed on Feb. 21, 2007.

(60) Provisional application No. 60/775,149, filed on Feb. 21, 2006.

(51) Int. Cl.
*C07D 471/00* (2006.01)
(52) U.S. Cl. ............................ 546/62; 546/64; 546/48
(58) Field of Classification Search .................... 546/48, 546/64, 62
See application file for complete search history.

(56) References Cited

U.S. PATENT DOCUMENTS

| | | | |
|---|---|---|---|
| 5,047,536 | A | 9/1991 | Nichols |
| 5,420,134 | A | 5/1995 | Nichols et al. |
| 5,597,832 | A | 1/1997 | Michaelides et al. |
| 5,681,947 | A | 10/1997 | Bergstrom et al. |
| 5,959,110 | A | 9/1999 | Nichols et al. |
| 6,194,423 | B1 | 2/2001 | Nichols et al. |
| 6,326,377 | B1 | 12/2001 | Lavielle et al. |
| 6,413,977 | B1 | 7/2002 | Nichols et al. |
| 6,916,823 | B2 | 7/2005 | Mailman et al. |
| 6,916,832 | B2 | 7/2005 | Nichols et al. |
| 7,220,754 | B2 | 5/2007 | Dijkstra et al. |
| 2005/0232870 | A1 | 10/2005 | Mailman et al. |
| 2007/0254906 | A1 | 11/2007 | Fernandes et al. |

FOREIGN PATENT DOCUMENTS
WO WO 2005/062894 7/2005

OTHER PUBLICATIONS

Cueva et al, J. Med. Chem. (2006) vol. 49 pp. 6848-6857, "trans-2,3-Dihydroxy-6a,7,8,12b-tetrahydro-6H-chromeno[3,4-c]isoquinoline: Synthesis, Resolution, and Preliminary Pharmacological Characterization of a New Dopamine D1 Receptor Full Agonist".*
Berge, S.M., Bighley, L.D., and Monkhouse, D.C., "Pharmaceutical Salts," J. Pharm. Sci., vol. 66, No. 1, 1977, pp. 1-19.
Bradley, K.C., Mullins, A.J., Meisel, R.L., and Watts, V.J., "Sexual Experience Alters D1 Receptor-Mediated Cyclic AMP Production in the Nucleus Accumbens of Female Syrian Hamsters," Synapse, vol. 53, No. 1, 2004, pp. 20-27.
Brewster, W.K., Nichols, D.E., Riggs, R.M., Mottola, D.M., Lovenberg, T.W., Lewis, M.H., and Mailman, R.B., "Trans-10, 11-Dihydroxy-5,6,6a,7,8, 12b-Hexahydrobenzo[a]phenanthridine: a Highly Potent Selective Dopamine D1 Full Agonist," J. Med. Chem., vol. 33, 1990, pp. 1756-1764.
Cueva, J.P., Giorgioni, G., Grubbs, R.A., Chemel, B.R., Watts, V.J., and Nichols, D.E., "Trans-2,3-Dihydroxy-6a,7,8,12b-Tetrahydro-6H-Chromeno[3,4-c]isoquinoline: Synthesis, Resolution, and Preliminary Pharmacological Characterization of a New Dopamine D1 Receptor Full Agonist," J. Med. Chem., vol. 49, 2006, pp. 6848-6857.
Gay, E.A., Urban, J.D., Nichols, D.E., Oxford, G.S., and Mailman, R.B., "Functional Selectivity of $D_2$ Receptor Ligands in a Chinese Hamster Ovary $hD_{2L}$ Cell Line: Evidence for Induction of Ligand-Specific Receptor States," Molecular Pharmacology, vol. 66, No. 1, 2004, pp. 97-105.
Gilmore, J.H., Watts, V.J., Lawler, C.P., Noll, E.P., Nichols, D.E., and Mailman, R.B., "'Full' Dopamine D1 Agonists in Human Caudate: Biochemical Properties and Therapeutic Implications," Neuropharmacology, vol. 34, No. 5, 1995, pp. 481-488.
Johnson, D.E., Ochieng, J., and Evans, S.L., "The Growth Inhibitory Properties of a Dopamine Agonist (SKF 38393) on MCF-7 Cells," Anti-Cancer Drugs, vol. 6, No. 3, 1995, pp. 471-474.
Knoerzer, T.A., Nichols, D.E., Brewster, W.K., Watts, V.J., Mottola, D., and Mailman, R.B., "Dopaminergic Benzo[a]phenanthridines: resolution and pharmacological evaluation of the Enantiomers of Dihydrexidine, the Full Efficacy D1 Dopamine Receptor Agonist," J. Med. Chem., vol. 37, No. 15, 1994, pp. 2453-2460.
Michaelides, M.R., Hong, Y., DiDomenico, Jr., S., Bayburt, E.K., Asin, K.E., Britton, D.R., Lin, C.W., and Shiosaki, K., "Substituted Hexahydrobenzo[f]thieno[c]quinolines as Dopamine D1-Selective Agonists: Synthesis and Biological Evaulation in Vitro and In Vivo," J. Med. Chem., vol. 40, 1997, pp. 1585-1599.
Pitfield, S.E., Bryant, I., Penington, D.J., Park, G., and Riese II, D.J., "Phosphorylation of ErbB4 on Tyrosine 1056 is Critical for ErbB4 Coupling to Inhibition of Colony Formation by Human Mammary Cell Lines," Oncology Research Featuring Preclinical and Clinical Cancer Therapeutics, vol. 16, No. 4, 2006, pp. 179-193.
Watts, V.J., Lawler, C.P., Gonzales, A.J., Zhou, Q.Y., Civelli, O., Nichols, D.E., and Mailman, R.B., "Spare Receptors and Intrinsic Activity: Studies with D1 Dopamine Receptor Agonists," Synapse, vol. 21, No. 2, 1995, pp. 177-187.
International Search Report for International Application No. PCT/US2007/062481, Jun. 6, 2008, 17 pages.
Grubbs, Russell A., Synthesis of Novel Dopaminergic Ligands: A Bioisosteric Approach (Aug. 2000) (unpublished Ph.D. Thesis, Purdue University), microformed on UMI Microform 3018202 (2001) (Bell & Howell Information and Learning Company).

* cited by examiner

*Primary Examiner* — Andrew D Kosar
*Assistant Examiner* — Raymond Covington
(74) *Attorney, Agent, or Firm* — Barnes & Thornburg LLP

(57) ABSTRACT

Optionally substituted chromenoisoquinolines and analogs and derivatives thereof are described herein. In addition, syntheses of these compounds are described herein. In addition, uses of these compounds as dopamine receptor binding compounds are described herein.

45 Claims, 5 Drawing Sheets

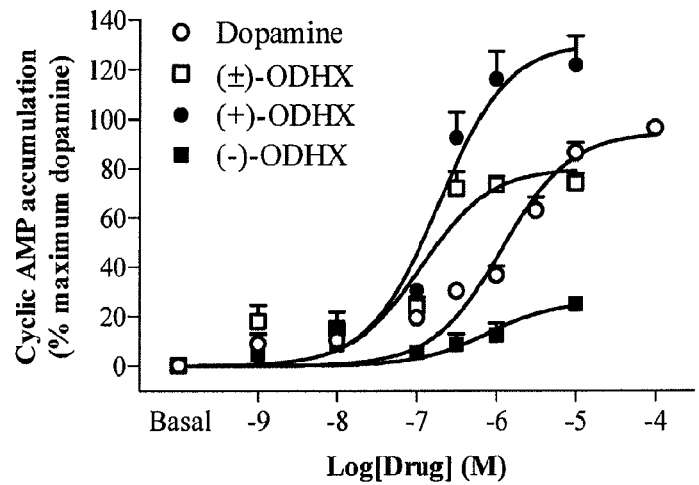
Figure 3A
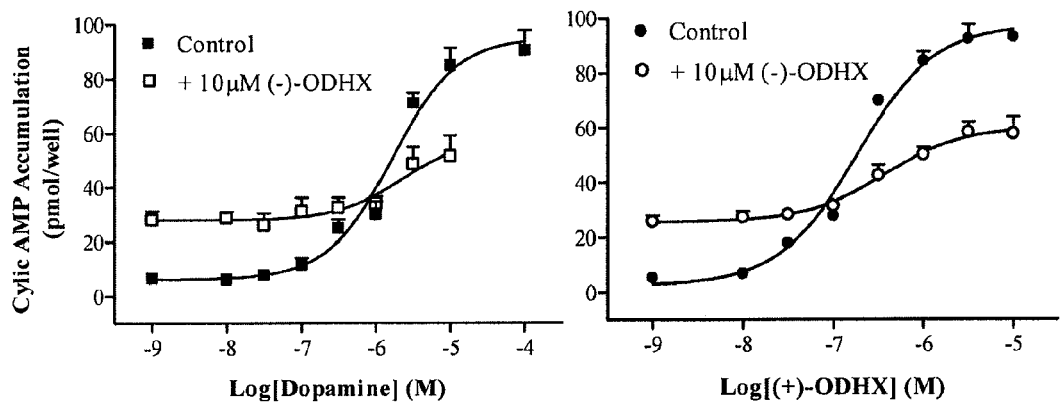
Figure 3B  Figure 3C

TRANS-FUSED CHROMENOISOQUINOLINES SYNTHESIS AND METHODS FOR USE

The present application is a continuation of International Patent Application Serial No. PCT/US2007/062481, filed Feb. 21, 2007, the entirety of which is incorporated by reference herein, which application claims the benefit of U.S. Provisional Patent Application Ser. No. 60/775,149, filed Feb. 21, 2006, the entirety of which is incorporated by reference herein.

GOVERNMENT RIGHTS

This invention was made with government support under Grant No. MH 042705 awarded by The National Institutes of Mental Health. The United States Government has certain rights in this invention.

TECHNICAL FIELD

The present invention pertains to optionally substituted chromenoisoquinolines and analogs and derivatives thereof, syntheses thereof, and uses therefor.

BACKGROUND

Dopamine is an important neurotransmitter in the central nervous system (CNS), where it has been shown to be involved with motor function, perception, arousal, motivation and emotion. Accordingly, dopamine dysfunction has been shown to play an important role in a number of CNS-related disorders including psychotic disorders, movement disorders, schizophrenia, Parkinson's disease, drug abuse, eating disorders, cognition and memory disorders, depression, sexual dysfunction, and others. Dopamine has also been shown to play an important role in the peripheral nervous system, where it has been associated with the control of blood to the kidneys and in autonomic ganglion transmission.

Dopamine receptors in the CNS have traditionally been divided into two general categories, designated $D_1$ and $D_2$ receptors, based on biochemical and pharmacological differences between the two receptor types. Further, additional dopamine receptors have been identified and defined through molecular cloning techniques. For example, the $D_3$ and $D_4$ receptors have been described and are classified as $D_2$-like, and the $D_5$ receptor has been described and exhibits $D_1$-like receptor pharmacology.

Conformationally restricted analogs of dopamine have also been reported in U.S. Pat. Nos. 5,047,536, 5,420,134, 6,194,423, 6,413,977, and 5,597,832, the disclosures of which are incorporated herein by reference.

SUMMARY OF THE INVENTION

Optionally substituted chromenoisoquinolines of formula (I) are described herein:

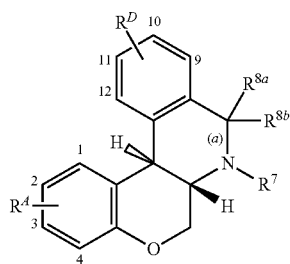

I wherein
$R^A$ represents from 1 to 4 substituents each independently selected from the group consisting of hydrogen, halo, optionally substituted alkyl, amino, acylamino, optionally substituted alkylsulfonyl, aminosulfonyl, nitro, and —OR³, where $R^{13}$ is alkyl, acyl, alkanoyl, aryloyl, a phenol protecting group, or a prodrug group, each of which is optionally substituted; or $R^A$ represents from 2 to 4 substituents, where 2 of said substituents are adjacent and are taken together to form an optionally substituted carbocyclic or an optionally substituted heterocyclic ring, and each other substituent is independently selected from the group consisting of hydrogen, halo, optionally substituted alkyl, amino, acylamino, optionally substituted alkylsulfonyl, aminosulfonyl, nitro, and —OR³, where $R^{13}$ is alky, acyl, alkanoyl, aryloyl, a phenol protecting group, or a prodrug group, each of which is optionally substituted;

$R^D$ represents 1-4 substituents each independently selected from the group consisting of hydrogen and a radical —(CH₂)ₘZ, where m is an integer from 0-6 and Z is selected from the group consisting of halogen, hydroxy, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or $R^D$ represents 2-4 substituents where 2 of said substituents are adjacent substituents and are taken together with the attached carbons to form an optionally substituted carbocycle or an optionally substituted heterocycle, and the remaining 2 substituents are each independently selected from the group consisting of hydrogen and a radical —(CH₂)ₘZ, where m is an integer from 0-6 and Z is selected from the group consisting of halogen, hydroxy, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl;

$R^7$ is selected from the group consisting of hydrogen and a group —(CH₂)ₘ'Z', where m' is an integer from 0-6 and Z' is selected from the group consisting of hydrogen, halogen, hydroxy, formyl, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl;

$R^{8a}$ is hydrogen; and $R^{8b}$ is selected from the group consisting of hydrogen, hydroxy, optionally substituted alkyl, optionally substituted alkoxy, and optionally substituted amino; or $R^{8a}$ and $R^{8b}$ are taken together to form a double-bonded oxygen; and represents a single bond or a double bond; providing that when (a) is a double bond, the group $R^{8a}$ is absent.

The compounds described herein may be combined with pharmaceutically active carriers, diluents, and/or excipients to prepare pharmaceutical compositions.

The compounds described herein may be useful for treating dopamine-related disorders by binding to dopamine receptors. The compounds described herein may be either full agonists, partial agonists, or antagonists at the dopamine receptor. In addition, the compounds described herein may exhibit functional selectivity at one or more dopamine receptors.

Syntheses of optionally substituted chromenoisoquinolines, and analogs and derivatives thereof are also described herein.

Methods for treating dopamine related dysfunction that include the compounds and/or pharmaceutical compositions are also described herein.

BRIEF DESCRIPTION OF THE DRAWINGS

The above-mentioned aspects of the present invention and the manner of obtaining them will become more apparent and the invention itself will be better understood by reference to the following description of the embodiments of the invention taken in conjunction with the accompanying drawings, wherein:

FIG. 3A is a graph showing the dose-dependent stimulation of cyclic AMP at the endogenous dopamine $D_1$ receptor in MCF7 cells;

FIG. 3B is a graph showing the dose-dependent stimulation of cyclic AMP at the endogenous dopamine $D_1$ receptor in MCF7 cells for dopamine in the absence and presence of (−)-ODHX;

FIG. 3C is a graph showing the dose-dependent stimulation of cyclic AMP at the endogenous dopamine $D_1$ receptor in MCF7 cells for (+)-ODHX in the absence and presence of (−)-ODHX;

DETAILED DESCRIPTION

Figure 1:
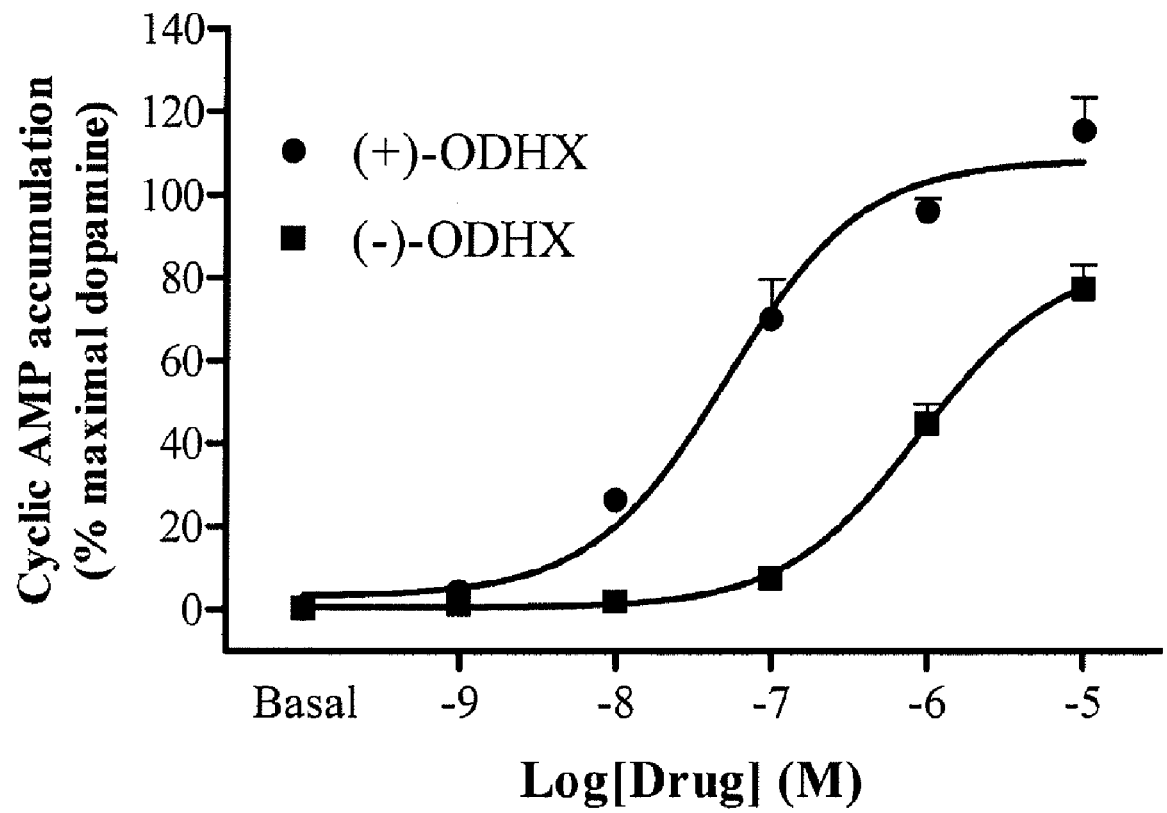
FIG. 1 is a graph showing dose-response curves for dopamine $D_1$ receptor-mediated stimulation of cyclic AMP accumulation.

In one embodiment, compounds of formula (I) are described:

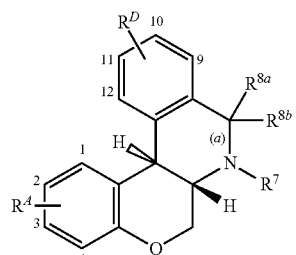

wherein $R^A$ represents from 1 to 4 substituents each independently selected from the group consisting of hydrogen, halo, optionally substituted alkyl, amino, acylamino, optionally substituted alkylsulfonyl, aminosulfonyl, nitro, and —$OR^{13}$, where $R^{13}$ is alkyl, acyl, alkanoyl, aryloyl, a phenol protecting group, or a prodrug group, each of which is optionally substituted; or $R^A$ represents from 2 to 4 substituents, where 2 of said substituents are adjacent and are taken together to form an optionally substituted carbocyclic or an optionally substituted heterocyclic ring, and each other substituent is independently selected from the group consisting of hydrogen, halo, optionally substituted alkyl, amino, acylamino, optionally substituted alkylsulfonyl, aminosulfonyl, nitro, and —$OR^{13}$, where $R^{13}$ is alkyl, acyl, alkanoyl, aryloyl, a phenol protecting group, or a prodrug group, each of which is optionally substituted;

$R^D$ represents 1-4 substituents each independently selected from the group consisting of hydrogen and a radical —$(CH_2)_m Z$, where m is an integer from 0-6 and Z is selected from the group consisting of halogen, hydroxy, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, optionally substituted phenoxy, and optionally substituted heteroaryl; or $R^D$ represents 2-4 substituents where 2 of said substituents are adjacent substituents and are taken together with the attached carbons to form an optionally substituted carbocycle or an optionally substituted heterocycle, and the remaining 2 substituents are each independently selected from the group consisting of hydrogen and a radical —$(CH_2)_m Z$, where m is an integer from 0-6 and Z is selected from the group consisting of halogen, hydroxy, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—(C$_1$-C$_6$ alkyl)alkylcarbonylaminoalkyl, cyano, nitro, C$_1$-C$_6$ alkylsulfonyl, optionally substituted phenyl, optionally substituted phenoxy, and optionally substituted heteroaryl;

R$^7$ is selected from the group consisting of hydrogen and a group —(CH$_2$)$_{m'}$Z', where m' is an integer from 0-6 and Z' is selected from the group consisting of hydrogen, halogen, hydroxy, formyl, C$_1$-C$_6$ alkanoyloxy, optionally substituted benzoyloxy, C$_1$-C$_6$ alkyl, C$_1$-C$_6$ alkoxy, C$_3$-C$_8$ cycloalkyl, C$_3$-C$_8$ cycloalkoxy, C$_2$-C$_6$ alkenyl, C$_2$-C$_6$ alkynyl, C$_1$-C$_6$ haloalkyl, C$_1$-C$_6$ haloalkoxy, C$_3$-C$_8$ halocycloalkyl, C$_3$-C$_8$ halocycloalkoxy, amino, C$_1$-C$_6$ alkylamino, (C$_1$-C$_6$ alkyl)(C$_1$-C$_6$ alkyl)amino, alkylcarbonylamino, N—(C$_1$-C$_6$ alkyl)alkylcarbonylamino, aminoalkyl, C$_1$-C$_6$ alkylaminoalkyl, (C$_1$-C$_6$ alkyl)(C$_1$-C$_6$ alkyl)aminoalkyl, alkylcarbonylaminoalkyl, N—(C$_1$-C$_6$ alkyl)alkylcarbonylaminoalkyl, cyano, nitro, C$_1$-C$_6$ alkylsulfonyl, optionally substituted phenyl, optionally substituted phenoxy, and optionally substituted heteroaryl;

R$^{8a}$ is hydrogen; and R$^{8b}$ is selected from the group consisting of hydrogen, hydroxy, optionally substituted alkyl, optionally substituted alkoxy, and optionally substituted amino; or R$^{8a}$ and R$^{8b}$ are taken together to form a double-bonded oxygen; and represents a single bond or a double bond; providing that when (a) is a double bond, the group R$^{8a}$ is absent.

As used herein, the term "phenol protecting group" refers to substituents on the phenolic oxygen which prevent undesired reactions and degradations during synthesis and which can be removed later without effect on other functional groups on the molecule. Illustrative phenol protecting groups include ethers, such as methyl, isopropyl, t-butyl, cyclopropylmethyl, cyclohexyl, allyl, and the like ethers; alkoxyalkyl ethers such as methoxymethyl, methoxyethoxymethyl, and the like ethers; alkylthioalkyl ethers such a methylthiomethyl ethers; tetrahydropyranyl ethers; arylalkyl ethers such as benzyl, o-nitrobenzyl, p-methoxybenzyl, 9-anthrylmethyl, 4-picolyl, and the like ethers; trialkylsilyl ethers such as trimethylsilyl, triethylsilyl, t-butyldimethylsilyl, t-butyldiphenylsilyl, and the like ethers; esters, such as alkyl, aryl, and like esters including acetates, propionates, n-butyrates, isobutyrates, pivaloate, trimethylacetates, benzoates, and the like; carbonates, such as methyl, ethyl, 2,2,2-trichloroethyl, 2-trimethylsilylethyl, vinyl, benzyl, and the like carbonates; and carbamates, such as methyl, isobutyl, phenyl, benzyl, dimethyl, and the like carbamates.

As used herein, the term "prodrug group" includes alkanoyl; haloalkanoyl; alkenoyl; cycloalkanoyl; cycloalkylalkanoyl; optionally substituted aryloyl, optionally substituted arylalkanoyl, optionally substituted hetero-arylalkanoyl having one to three heteroatoms selected from oxygen, sulfur, and nitrogen in the heteroaryl moiety. Optional substitutions include but are not limited to halogen, cyano, trifluoromethanesulphonyloxy, optionally substituted alkyl, and/or optionally substituted alkoxy.

Illustrative examples of alkanoyl include but are not limited to propanoyl, isopropanoyl, butanoyl, 2-methylpropanoyl, pentanoyl, 3-methyl-butanoyl, pivaloyl, n-hexanoyl, n-heptanoyl, n-octanoyl, n-nonanoyl, n-decanoyl, palmitoyl, stearoyl, eicosanoyl, and the like.

Illustrative examples of alkenoyl include but are not limited to acryloyl, methacryloyl, linoleoyl, linolenoyl, and the like.

Illustrative examples of cycloalkanoyl include but are not limited to cyclopropanoyl, cyclobutanoyl, cyclopentanoyl, cyclohexanoyl, and the like.

Illustrative examples of cycloalkylalkanoyl include but are not limited to cyclopropylacetyl, cyclohexylacetyl, cyclopropylhexanoyl, cyclopropylpalmitoyl, and the like.

Illustrative examples of aryloyl include but are not limited to optionally substituted benzoyl, 1-naphthoyl, 2-naphthoyl, and the like. Optional substitutions include but are not limited to halo, cyano, trifluoromethanesulphonyloxy, alkyl, alkoxy, and the like, such as m-methoxybenzoyl, p-trifluoromethoxybenzoyl, p-chlorobenzoyl, 3,4,5-trimethoxybenzoyl, p-cyanobenzoyl, 3-chloro-1-napthoyl, and the like.

Illustrative examples of arylalkanoyl include but are not limited phenylacetyl, p-chlorophenylacetyl, p-trifluoromethoxyphenylacetyl, phenylhexanoyl, and the like.

In another embodiment, optionally substituted chromenoisoquinolines of formula (Ia) are described herein:

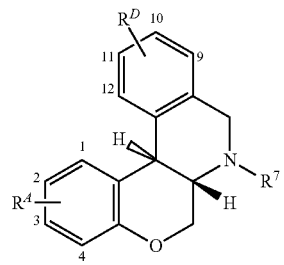

Ia wherein R$^A$, R$^D$, and R$^7$ are as defined in formula (I)

In another embodiment, optionally substituted chromenoisoquinolines of formula (Ib) are described herein:

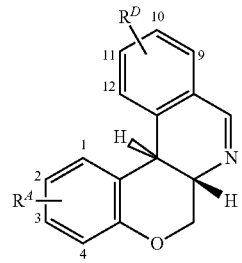

Ib wherein R$^A$, R$^D$, and R$^7$ are as defined in formula (I).

In another embodiment, optionally substituted chromenoisoquinolines of formula (Ic) are described herein:

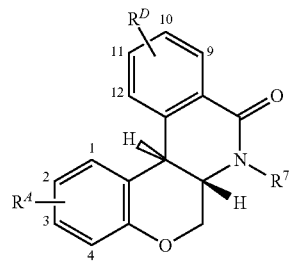

Ic wherein R$^A$, R$^D$, and R$^7$ are as defined in formula (I).

In another embodiment, optionally substituted chromenoisoquinolines of formula (Id) are described herein:

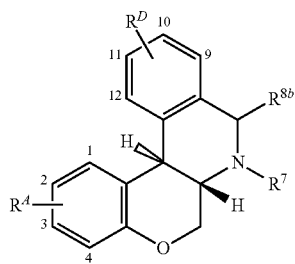

wherein $R^A$, $R^D$, $R^7$ and $R^{8b}$ are as defined in formula (I).

In another embodiment, optionally substituted chromenoisoquinolines of formula (Ie) are described herein:

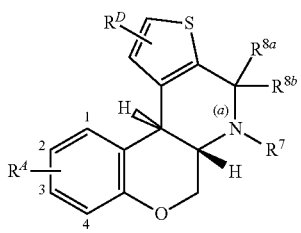

wherein $R^A$, $R^D$, $R^7$, $R^{8a}$ and $R^{8b}$ are as defined in formula (I). The chromenoisoquinolines of formula Ie have a thiophene moiety replacing the phenyl moiety.

In another embodiment, compounds of formula (II) are described:

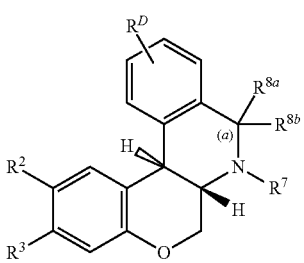

wherein $R^2$ and $R^3$ are each independently selected from the group consisting of hydrogen, halo, optionally substituted alkyl, amino, acylamino, optionally substituted alkylsulfonyl, aminosulfonyl, nitro, and —$OR^3$, where $R^{13}$ is alkyl, acyl, alkanoyl, aryloyl, a phenol protecting group, or a prodrug group, each of which is optionally substituted; or $R^2$ and $R^3$ are taken together to form an optionally substituted carbocyclic or an optionally substituted heterocyclic ring. $R^D$, $R^7$, $R^{8a}$ and $R^{8b}$ are as defined in formula (I).

In a further embodiment, compounds of formula (IIa) are described:

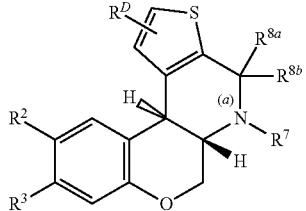

wherein $R^2$ and $R^3$ are each independently selected from the group consisting of hydrogen, halo, optionally substituted alkyl, amino, acylamino, optionally substituted alkylsulfonyl, aminosulfonyl, nitro, and —$OR^3$, where $R^{13}$ is alkyl, acyl, alkanoyl, aryloyl, a phenol protecting group, or a prodrug group, each of which is optionally substituted; or $R^2$ and $R^3$ are taken together to form an optionally substituted carbocyclic or an optionally substituted heterocyclic ring. $R^D$, $R^7$, $R^{8a}$ and $R^{8b}$ are as defined in formula (I).

In another embodiment, compounds of formula (III) are described:

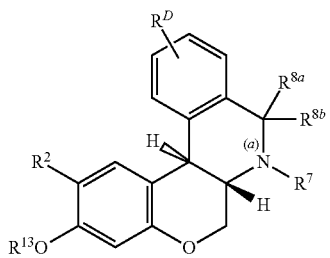

wherein $R^{13}$ is in each instance independently selected from the group consisting of alkyl, acyl, alkanoyl, aryloyl, a phenol protecting group, or a prodrug group, each of which is optionally substituted; each $R^{13}$ is taken with the other to form an optionally substituted oxygen heterocyclic ring. $R^D$, $R^7$, $R^{8a}$ and $R^{8b}$ are as defined in formula (I).

In one aspect of the compounds of formula (III), one of $R^{13}$ is hydrogen, and the other of $R^{13}$ is a prodrug group. In another aspect of the compounds of formula (II), each group $R^{13}$ is a prodrug group, but the two prodrug groups are different. The monoester prodrugs and/or differential diester prodrugs of compounds of formula (III) may be prepared according to the procedure described in U.S. Pat. No. 7,220,754, the disclosure of which is incorporated herein by reference.

In another embodiment, compounds of formulae IVa and IVb are described:

IVa

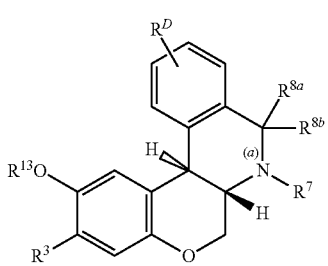

IVb wherein $R^2$ and $R^3$ are selected from the group consisting of hydrogen, halo, optionally substituted alkyl, such as haloalkyl, and the like, amino, acylamino, optionally substituted alkylsulfonyl, such as haloalkylsulfonyl, and the like, aminosulfonyl, or nitro; and $R^{13}$ is selected from the group consisting of hydrogen, alkyl, acyl, a phenol protecting group, or a prodrug group. $R^D$, $R^7$, $R^{8a}$ and $R^{8b}$ are as defined in formula (I).

In one aspect of the compounds of formulae II, III, IVa, and IVb, both $R^{8a}$ and $R^{8b}$ are hydrogen; and bond (a) is a single bond. In another aspect of the compounds of formulae II, III, IVa, and IVb, $R^{8a}$ is absent; and bond (a) is a double bond. In another aspect of the compounds of formulae II, III, IVa, and IVb, $R^{8a}$ is absent; $R^{8b}$ is alkyl; and bond (a) is a double bond. In another aspect of the compounds of formulae II, III, IVa, and IVb, $R^{8a}$ is absent; $R^{8b}$ is hydroxy, optionally substituted alkoxy, or optionally substituted amino; and bond (a) is a double bond. In another aspect of the compounds of formulae II, III, IVa, and IVb, $R^{8a}$ and $R^{8b}$ are taken together to form a double-bonded oxygen; and bond (a) is a single bond.

It is appreciated that the compounds described herein include two or more chiral centers, including the two chiral centers that define the trans ring fusion of the chromenoisoquinoline, defined by carbons (C-6a) and (C-12b) and denoted by bond (b) in the following formulae:

lels the relative activity of enantiomers reported for other conformationally restricted analogs of dopamine.

In one embodiment, the compounds described herein include antagonists at dopamine receptors. Without being bound by theory, it is believed that compounds of the formulae described herein show antagonistic behavior at dopamine receptors when $R^4$ includes only one hydroxy group, or a protected or prodrug variant thereof. In one aspect, the hydroxy group, or the protected or prodrug variant thereof is located at carbon (C-2). In another aspect, the hydroxy group, or the protected or prodrug variant thereof is located at carbon (C-3). In another aspect, a group selected from hydrogen, halo, optionally substituted alkyl, such as haloalkyl, and the like, amino, acylamino, optionally substituted alkylsulfonyl, such as haloalkylsulfonyl, and the like, aminosulfonyl, or nitro is located at carbon (C-2). In another aspect, a group selected from hydrogen, halo, optionally substituted alkyl, such as haloalkyl, and the like, amino, acylamino, optionally substituted alkylsulfonyl, such as haloalkylsulfonyl, and the like, aminosulfonyl, or nitro is located at carbon (C-3).

In another embodiment, the compounds described herein are full or partial agonists at dopamine receptors. Without being bound by theory, it is believed that compounds of the formulae described herein show full or partial agonist behavior at dopamine receptors when $R^4$ includes two hydroxy groups, or protected or prodrug variants thereof. In one aspect, the hydroxy groups, or protected or prodrug variants thereof, are located at carbons (C-2) and (C-3) as shown in formula (I).

In another embodiment, the compounds described herein may show functional selectivity at one or more dopamine receptors, such as the $D_2$ receptor as described by Gay et al. in "Functional selectivity of $D_2$ receptor ligands in a Chinese hamster ovary $hD_{2L}$ cell line: evidence for induction of ligand-specific receptor states," *Mol. Pharmacol.* 66(1):97-105 (2004), the disclosure of which is incorporated herein by reference. Functional selectivity is the property where a com-

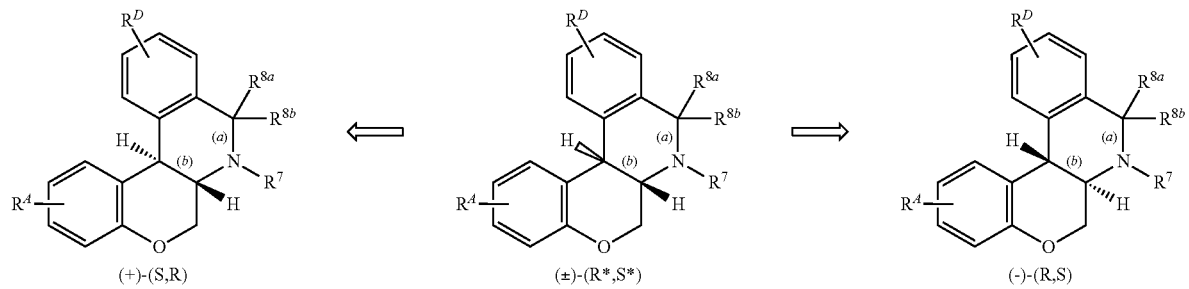

It is to be understood that the compounds described herein include both enantiomers in a variety of mixtures, including racemic mixtures. It is also to be understood that the compounds described herein include each enantiomer individually, including each enantiomer in substantially optically pure form. Accordingly, the (R*,S*) solid wedge/hollow wedge relative stereochemistry shown in the compound formulae described herein refers both collectively and individually to such mixtures and such enantiomerically pure forms.

It is also appreciated that one enantiomer may be more active than the other in certain biological and/or pharmacological evaluations. For example, it is understood that the (6aS,12bR) enantiomer has higher affinity for dopamine receptors than its enantiomer. This differential activity paralpound described herein may operate as a full agonist, a partial agonist, or even an antagonist at a pre-determined receptor for each of the G-proteins coupled to that receptor. Thus, if a pre-determined receptor has coupled to it two or more signals, such as a $G_{i/o}$ and a $G_q$ protein, the compound may operate as an agonist for one protein, and an antagonist for the other protein. It is understood that the endogenous ligand dopamine is a full agonist for each coupled G-protein.

In another embodiment, pharmaceutical compositions are described herein. Such pharmaceutical compositions include one or more of the compounds described herein, or a pharmaceutically acceptable salt or hydrate thereof, and a pharmaceutically acceptable carrier, diluent, or excipient therefor.

The term "pharmaceutically acceptable" includes those salts, carriers, diluents, and excipients that are within the scope of sound medical judgment, suitable for use in contact with the tissues of humans and lower animals without undue toxicity, irritation, allergic response and the like, and are commensurate with a reasonable benefit/risk ratio, effective for their intended use in the treatment of psychological, neurological, cardiovascular and addictive behavior disorders.

The term "pharmaceutically acceptable carriers" includes nontoxic, inert solid, semi-solid or liquid filler, diluent, encapsulating material or formulation auxiliary of any type. Illustrative examples of the materials that can serve as pharmaceutically-acceptable carriers are sugars, such as lactose, glucose and sucrose: starches, such as corn starch and potato starch; cellulose and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringers solution; ethyl alcohol and phosphate buffer solutions, as well as other non-toxic compatible substances used in pharmaceutical formulations. Wetting agents, emulsifiers and lubricants, such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Illustrative examples of pharmaceutically-acceptable antioxidants include water-soluble antioxidants, such as ascorbic acid, cysteine hydrochloride, sodium bisulfite, sodium metabisulfite, sodium sulfite, and the like; oil soluble antioxidants, such as ascorbyl palmitate, butylated hydroxyanisole (BHA), butylated hydroxytoluene (BHT), lecithin, propyl gallate, alpha-tocopherol and the like; and the metal chelating agents, such as citric acid, ethylenediamine tetraacetic acid (EDTA), sorbitol, tartaric acid, phosphoric acid and the like. In one aspect, the pharmaceutically acceptable carrier, diluent, or excipient are those generally regarded as safe (GRAS).

In another embodiment, the compounds described herein include acid addition salts to at least one amino group, such as the ring nitrogen adjacent to the ring fusion. Such acid addition salts include salts of mineral acids salts of organic acids, salts of sulphonic acids, and the like.

Pharmaceutically acceptable salts are well known in the art, as exemplified, for example, by S. M. Berge et al., who describe pharmaceutically-acceptable salts in detail in J. Pharm. Sci., 66: 1-19, 1977. The salts may be prepared in situ during the final isolation and purification of the compounds of Formula (I), or separately by reacting the free base function with a suitable organic, mineral, sulfonic, or like acid. Representative acid-addition salts include hydrochloride, hydrobromide, sulfate, bisulfate, acetate, oxalate, valerate, oleate, palmitate, stearate, laurate, borate, benzoate, lactate, phosphate, toluenesulfonate, methanesulfonate, citrate, maleate, fumarate, succinate, tartrate, ascorbate, glucoheptonate, lactobionate, lauryl sulfate salts, and the like.

In another embodiment, the compounds described herein are converted into carbamate derivatives. In one aspect, the carbamates are formed from the ring nitrogen. In another aspect of compounds that include one or more phenolic hydroxyl groups, the carbamates may be formed from one or more of such phenolic hydroxyl groups. Illustrative examples of pharmaceutically acceptable, nontoxic carbamates of the compounds described herein include lower alkyl carbamates, i.e. $C_1$-$C_4$ or $C_1$-$C_6$ alkyl carbamates, aryl carbamates, and heterocyclic carbamates. Such lower alkyl carbamates may be straight- or branched-chain. Such carbamates of the compounds described herein may be prepared according to conventional methods.

In another embodiment, methods for treating dopamine-related disorders and/or dysfunctions are described herein. The methods include administering a therapeutically effective amount of one or more compounds and/or one or more pharmaceutical compositions described herein to a patient in need of relief or suffering from the dopamine-related disorders and/or dysfunctions.

The term "administering" includes systemic use, as when taken orally, parenterally, by inhalation spray, by nasal, rectal, or buccal routes, or topically in dosage form unit formulations containing conventional nontoxic pharmaceutically-acceptable carriers, adjuvants and vehicles.

The term "therapeutically effective amount" includes a sufficient amount of the compound described herein to treat dopamine-related disorders and/or dysfunctions at a reasonable benefit/risk ratio applicable to any medical treatment. However, it is to be understood that the total daily usage of the compounds and compositions of the present invention will be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known in the medical arts.

In one embodiment, the dopamine-related dysfunction treatable with the compounds and methods described herein includes the loss of striatal dopamine within the basal ganglia, the region of the mammalian brain that is involved with motor control. Such dopamine deficiency has been established as the fundamental deficit in Parkinson's disease, and primary to the etiology of that disease state and other movement disorders. It is appreciated that dopamine agonists, including $D_1$-selective agonists, and agonists that are selective to post-synaptic receptors may increase striatal dopamine levels and provide treatment for Parkinson's disease.

In another embodiment, the dopamine-related dysfunction treatable with the compounds and methods described herein includes an excess of dopamine in the brain, which has been identified as a cause of schizophrenia, a psychiatric illness involving disturbance of thought processes, hallucinations, and loss of touch with reality. In addition, chronic abuse of stimulants, such as amphetamines, known to enhance dopaminergic activity in the brain, can lead to a paranoid psychosis that is clinically indistinguishable from classic paranoid schizophrenia, further supporting this dopamine theory of schizophrenia. It is appreciated that dopamine antagonists, including $D_2$-selective antagonists, may decrease dopamine levels in the brain and provide treatment schizophrenia and other psychiatric illnesses.

In another embodiment, the dopamine-related dysfunction treatable with the compounds and methods described herein includes excess dopamine in the brain's reward system. It has been reported that animals trained to self-administer cocaine will increase their consumption of this drug after treatment with either a $D_1$ or a $D_2$ dopamine receptor antagonist, presumably in order to maintain the elevated dopamine levels responsible for the cocaine's euphorigenic and reinforcing properties. Similarly, it has been reported that dopamine $D_1$ agonists decrease food intake by rats, presumably by direct action of the drug on neural feeding mechanisms. It is appreciated that this interrelationship between dopamine and the brain's reward system might be useful for the treatment of substance abuse and other addictive behavior disorders, including cocaine addiction, nicotine addiction, and eating disorders by administering the dopaminergic agents described herein.

In another embodiment, the dopamine-related dysfunction treatable with the compounds and methods described herein includes a reduction in the central nervous system of certain biogenic amine neurotransmitters, such as dopamine, noradrenaline and serotonin, which may cause affective disorders, the most common psychiatric disorders in adults, characterized by changes in mood as the primary clinical manifestation. It is appreciated that the dopamine agonists described herein may be useful in treating such affective disorders.

In another embodiment, the dopamine-related dysfunction treatable with the compounds and methods described herein includes cognition and attention disorders. Animal studies support the role of dopamine in attention-related behaviors involving search and exploratory activity, distractibility, response rate, ability to discriminate, and the switching of attention. It is appreciated that the compounds described herein may be useful in treating such cognition and attention disorders.

In another embodiment, the dopamine-related dysfunction treatable with the compounds and methods described herein includes peripheral nervous system disorders, such as shock, hypertension, congestive heart failure, and acute renal failure. Stimulation of the peripheral $D_1$ receptors causes vasodilation, particularly in the renal and mesenteric vascular beds where large numbers of these receptors are found. However, simultaneous stimulation of peripheral $D_2$ receptors may cause emetic effects. Accordingly, the compounds described herein that exhibit peripheral $D_1$ agonist selectivity over peripheral $D_2$ receptors may be useful in treating such peripheral disorders.

The term "affective disorder" includes disorders that are characterized by changes in mood as the primary clinical manifestation, for example, depression.

The term "attention deficit disorder" includes pediatric neuropsychiatric disorders characterized by inattention, impulsivity, distractibility and sometimes hyperactivity, which replaces the less formal diagnoses of hyperactivity syndrome, hyperkinetic syndrome, minimal brain dysfunction and specific learning disability. The disorder is prevalent among pre-adolescent children and is reflected in poor school performance and social behavior and has been described in experimental reports of impaired perceptual, cognitive and motor function.

The term "cognitive impairment" includes a deficiency in any of the aspects of the cognitive (information processing) functions of perceiving, thinking and remembering.

The term "dopamine-related cardiovascular disorders" includes conditions which can be reversed or improved by administration of dopamine or a dopaminergic agent, either alone or in combination therapy with other classes of cardiovascular agents. The usefulness of dopaminergic agents in cardiovascular diseases, for example in the treatment of shock and congestive heart failure, is based on the known, but incompletely understood, role of dopamine in the cardiovascular system, especially the effects of dopamine on the heart and the ability of dopamine to produce vasoconstriction while maintaining blood flow through renal and mesenteric beds. Also included are other related, potential uses for dopaminergic agents which include, for example, use in renal failure.

The term "dopamine-related neurological and psychological disorders" includes behavioral disorders, such as psychoses and addictive behavior disorders; affective disorders, such as major depression; and movement disorders, such as Parkinson's Disease, Huntington's Disease and Gilles de la Tourette's syndrome; which have been linked, pharmacologically and/or clinically, to either insufficient or excessive functional dopaminergic activity In the CNS. Also included are miscellaneous indications for which dopaminergic agents have been found to be clinically useful. Examples of such indications include disorders characterized by vomiting, such as uremia, gastroenteritis, carcinomatosis, radiation sickness, and emesis caused by a variety of drugs; intractable hiccough and alcoholic hallucinosis.

The term "substance abuse" includes periodic or regular self-administration of psychoactive substances in the absence of medical indications and despite the presence of persistent or recurrent social, occupational, psychological or physical problems that the person knows are caused by or may be exacerbated by continued use of the substance.

In one embodiment, the total daily dose of the compounds described herein is administered to a patient in single or in divided doses, and may be in amounts, for example, from 0.01 to 50 mg/kg body weight or more, or from 0.1 to 30 mg/kg body weight. In one aspect, single dose compositions may contain such amounts or submultiples thereof to make up the daily dose. In another aspect, treatment regimens described herein include administration to a patient in need of such treatment from about 1 mg to about 1000 mg per day of the compounds in multiple doses or in a single dose.

The compounds described herein can be formulated in conventional drug dosage forms. Preferred doses of the present compounds depend on many factors, including the indication being treated, the route of administration, and the overall condition of the patient. For oral administration, for example, effective doses of the present compounds are expected to range from about 0.1 to about 50 mg/kg, more typically about 0.5 to about 25 mg/kg. Effective parenteral doses can range from about 0.01 to about 15 mg/kg of body weight, more typically from about 0.1 to about 5 mg/kg of body weight. In general, treatment regimens utilizing compounds in accordance with the present invention comprise administration of from about 1 mg to about 500 mg of the compounds per day in multiple doses or in a single dose.

The compounds described herein may be formulated in liquid dosage forms for oral administration, and may include pharmaceutically acceptable emulsions, microemulsions, solutions, suspensions, and syrups and elixirs containing conventional inert diluents, such as water. Such compositions may also comprise adjuvants such as wetting agents, emulsifying and suspending agents, sweetening, and flavoring agents. Injectable preparations of the compounds of the present invention can be formulated utilizing art-recognized procedures by dispersing or dissolving an effective dose of the compound in a parenterally acceptable diluent such as water, or more preferably isotonic sodium chloride solution. The parenteral formulations can be sterilized using conventional microfiltration techniques.

The compounds described herein may be formulated in solid compositions. Solid dosage forms for oral administration may include capsules, tablets, pills, powders, and granules. In such solid dosage forms the active compound may be admixed with at least one inert diluent, such as sucrose, lactose or starch, such dosage forms may also comprise, as is normal practice, additional substances other than inert diluents, e.g., tableting lubricants and other tableting aids, such as magnesium stearate and microcrystalline cellulose, binders and/or disintegrants. In the case of capsules, tablets and pills, the dosage forms may also comprise buffering agents. Tablets and pills may additionally be prepared with enteric coatings and other release-controlling coatings. Optionally powder compositions comprising an active compound of this invention and, for example, a starch or sugar carrier can be filled into gelatin capsules for oral administration. Other dosage forms of the compounds of the present invention can be formulated using art-recognized techniques in forms adapted for the specific mode of administration. Solid dosage forms may additionally be prepared with fillers in soft and hard-filled gelatin capsules using such excipients as lactose or milk sugar, as well as high molecular weight polyethylene glycols and the like.

In another embodiment, parenteral preparations are described. The term "parenteral" includes intravenous, intramuscular, intraperitoneal, intrastemal, subcutaneous, and intraarticular injection and infusion techniques.

In another embodiment, injectable preparations are described. Illustratively, sterile injectable aqueous or oleaginous suspensions may be formulated according to the conventional techniques using suitable dispersing or wetting agents and suspending agents. The sterile injectable preparation may also be a sterile injectable solution, suspension or emulsion in a nontoxic parenterally-acceptable diluent or solvent, for example, as a solution in 1,3-butanediol. Among the acceptable vehicles and solvents that may be employed are water, Ringers solution, U.S.P. and isotonic sodium chloride solution. In addition, sterile, fixed oils are conventionally employed as a solvent or suspending medium. For this purpose, any bland fixed oil may be employed, including synthetic mono- or diglycerides. Also, fatty acids, such as oleic acid, are used in the preparation of injectables.

The injectable formulation may be sterilized, for example, by filtration through a bacteria-retaining filter, or by incorporating sterilizing agents in the form of sterile solid compositions which may be dissolved or dispersed in sterile water or other sterile injectable medium lust prior to use.

In order to prolong the effect of a drug, the absorption of a drug may be slowed from subcutaneous or intramuscular injection. Illustratively, a suspension of the drug in a crystalline or amorphous material which has poor water solubility is injected. The rate of absorption of the drug becomes dependent on the rate of dissolution of the drug which is, in turn, dependent on the physical state of the drug, for example, the crystal size of the drug and its crystalline form. Another approach to delaying absorption of a drug is to administer the drug as a solution or suspension in oil. Injectable depot forms may also be made by forming microcapsule matrices of drugs and biodegradable polymers, such as with polylactide-polyglycolide oligomers and polymers. Depending on the ratio of drug to polymer and the composition of the polymer, the rate of drug release may be controlled by this method. Examples of other biodegradable polymers include poly-orthoesters and polyanhydrides. The depot injectables can also be made by entrapping the drug in liposomes or microemulsions which are compatible with body tissues.

Suppositories for rectal administration of the drug may be prepared by mixing the drug with a suitable non irritating excipient, such as cocoa butter and polyethylene glycol, both of which are solid at ordinary temperature, but liquid at the rectal temperature and will therefore melt in the rectum, releasing the drug.

In the case of capsules, tablets and pills, the dosage forms may also comprise buffering agents. Tablets and pills may additionally be prepared with enteric coatings and other release-controlling coatings.

If desired, the compounds described herein can be incorporated into slow release or targeted-delivery systems, such as polymer matrices, liposomes and microspheres.

The active compounds may also be in micro-encapsulated form with one or more excipients as noted above. The solid dosage forms of tablets, dragees, capsules, pills, and granules may be prepared with coatings and shells, such as enteric coatings and other coatings well-known in the pharmaceutical formulating art. They may optionally contain opacifying agents, and may also be of a composition that they release the active ingredient(s) only, or preferably, in a certain part of the intestinal tract, optionally in a delayed manner. Examples of embedding compositions which can be used include polymeric substances and waxes.

Dosage forms for topical or transdermal administration of a compound of this invention further include ointments, pastes, creams, lotions, gels, powders, solutions, sprays, inhalants or transdermal patches. The active component is admixed under sterile conditions with a pharmaceutically-acceptable carrier and any needed preservatives or buffers, as required. Ophthalmic formulations, ear drops, eye ointments, powders and solutions are also contemplated as being within the scope of this invention. Administration sublingually, from one or more of the above dosage forms, is also contemplated as a suitable mode of administration of the compounds of the invention.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to the compounds of this invention, excipients, such as lactose, talc, silicic acid, aluminum hydroxide, calcium silicates and polyamide powder, or mixtures of these substances. Sprays may additionally contain customary propellants. such as chlorofluorohydrocarbons or environmentally- and pharmaceutically-acceptable substitutes.

It is appreciated that transdermal patches may have the added advantage of providing controlled delivery of a compound to the body. Such dosage forms may be made by dissolving or dispersing the compound in the proper medium. Absorption enhancers may also be used to increase the flux of the compound across the skin. The rate may be controlled by either providing a rate-controlling membrane or by dispersing the compound in a polymer matrix or gel.

The compounds of the present invention may be administered alone or in combination or in concurrent therapy with other agents which affect the dopaminergic system, for example, L-dopa, amantadine, apomorphine or bromocryptine; and with cholinergic agents, for example, benztropine, biperiden, ethopromazine, procyclidine, trihexylphenidyl, and the like. The compounds of the present invention may also be co-administered with agents, for example, enzyme inhibitors, which block their metabolic transformation outside the CNS. The compounds of the present invention may also be co-administered with other antipsychotic agents. The term "antipsychotic agent" includes drugs used extensively in the symptomatic management of all forms of schizophrenia, organic psychosis, the manic phase of manic depressive illness and other acute idiopathic illnesses and occasionally used in depression or in severe anxiety.

In another embodiment, the compounds and processes shown in Scheme 1 are described. $R^A$-substituted benzaldehydes (2) are prepared by formylation of the corresponding $R^A$-substituted phenols (1), as illustrated in Scheme 1.

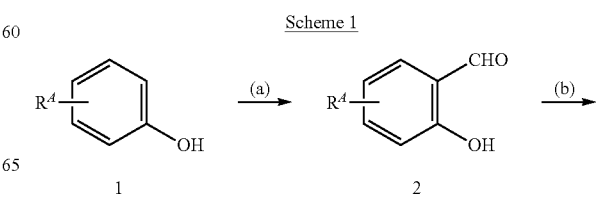

Scheme 1

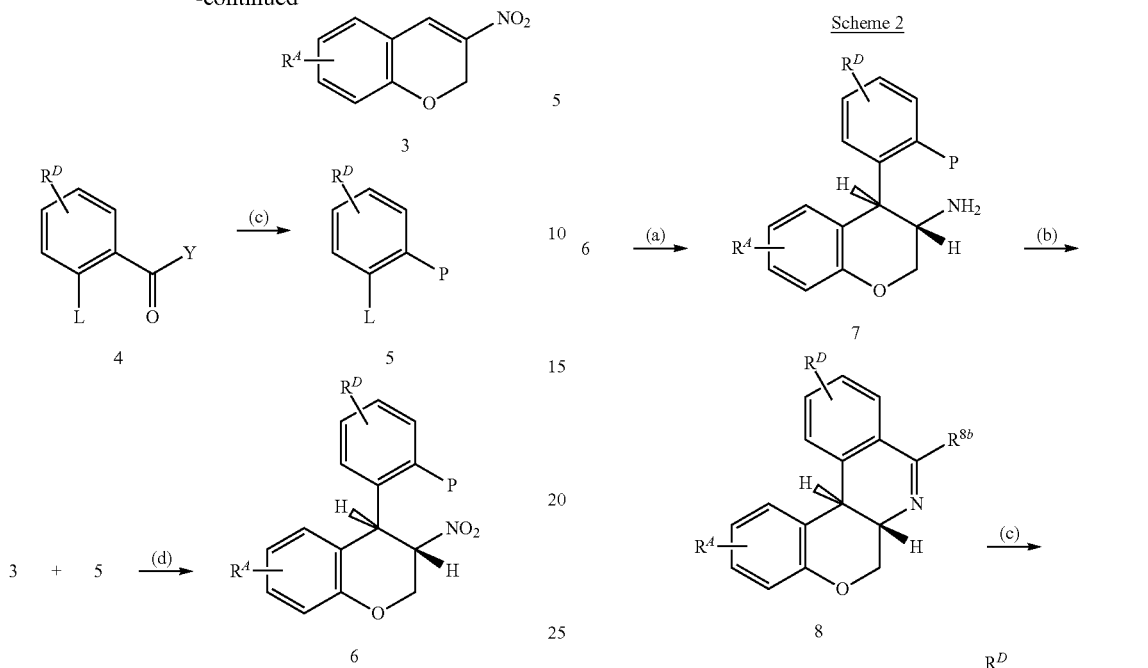

Benzaldehydes (2) are converted into nitro chromenes (3) with nitroethanol. $R^D$-substituted benzaldehydes, benzophenones, benzoic acids, and analogs and derivatives thereof (4), where Y is hydrogen, optionally substituted alkyl, hydroxy, optionally substituted alkoxy, halo, optionally substituted amino, and the like are protected as compounds (5), where P represents a protected form of the carbonyl, carboxylic acid, or analog or derivative thereof. In one illustrative aspect, Y is hydrogen or optionally substituted alkyl, and the protecting group is an acetal, ketal, or like protecting group. In another illustrative aspect, Y is hydroxy, and the protecting group is a carboxylic acid protecting group, such as an ester, amide, oxazoline, and the like. Other illustrative carbonyl and/or carboxylic protecting groups are described by Greene & Wuts in "Protective Groups in Organic Synthesis," 2d edition, John Wiley & Sons, Inc. New York (1991), the disclosure of which in its entirety is incorporated herein by reference.

Protected derivatives (5) include a group L that may be used to generate an anion at the corresponding carbon atom, including but not limited to hydrogen, halo, such as chloro, bromo, and iodo, and the like. Anion generation may be performed by for example transmetallation, lithiation, copper-lithiation, Grignard reagent formation, ortho lithiation, and the like. Once formed, anions of derivatives (5) are reacted with nitro chromenes (3) to prepare compounds (6) that include the trans relative stereochemistry of the nitro and phenyl groups. The relative stereochemistry of the two newly created chiral centers may be established using spectroscopic techniques, including one and two dimensional nuclear magnetic resonance.

In another embodiment, anions of derivatives (5) are reacted with nitro chromenes (3) to prepare compounds (6) in the presence of chiral auxiliaries that are capable of inducing asymmetry into compounds (6) and provide the optically active products rather than racemic products. In another embodiment, a chiral auxiliary is included on the anions of derivatives (5) and/or on the nitro chromenes (3) and provide the optically active products rather than racemic products.

In another embodiment, the compounds and processes shown in Scheme 2 are described, Compounds (6) are reduced to prepare amines (7), where P is a protected carbonyl group, such as a protected aldehyde or protected optionally substituted ketone.

It is appreciated that the carbonyl protecting group P of compounds (5), (6), and (7) is sufficiently unreactive such that it is not removed by the reaction conditions used in the processes described herein to prepare compound (7). It has been observed that loss of the aldehyde protecting group prior to the isolation of compound (7) may result in ring closure and subsequent aromatization of the nitrogen-containing heterocycle. Accordingly, carbonyl protected amines (7) are deprotected, and the resulting imines (8) are prepared by cyclization, where $R^{8b}$ is illustratively hydrogen or optionally substituted alkyl. It is also appreciated that the deprotecting and reducing conditions used are such that epimerization of the carbon adjacent to the nitro group does not occur. Imines (8) are reduced to chromenoisoquinolines (9). It is to be understood that variations of the processes described herein are contemplated, including that the group $R^A$ and/or the group $R^D$ may be converted into alternate groups. For example, the group $R^A$ may represent one or more protected derivatives, such as hydroxy, amino, and the like. Such protecting groups may be removed to provide the compounds (9) including free hydroxy, amino, and other like groups. It is appreciated that like conversions may be performed on the group $R^D$.

In another embodiment, the compounds and processes shown in Scheme 3 are described. Compounds (6) are deprotected to form carboxylic acid analogs or derivatives (10), where $L^2$ is a leaving group, such as halo, optionally substituted alkoxy, optionally substituted acyloxy, optionally substituted amino, and the like.

Scheme 3

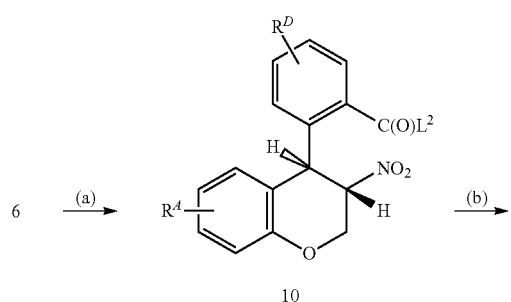

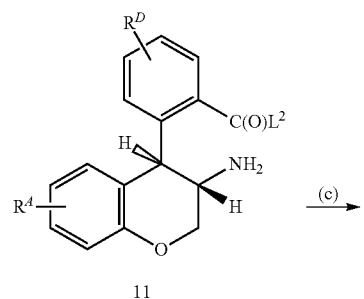

Compounds (10) are reduced to form amines (11). It is appreciated that the deprotecting and reducing conditions used are such that epimerization of the carbon adjacent to the nitro group does not occur. Amines (11) are cyclized to amides (12), which are reduced to chromenoisoquinolines (9). It is appreciated that in variations of the processes described herein, the group $R^A$ and/or the group $R^D$ may be converted into alternate groups. For example, the group $R^A$ may represent one or more protected derivatives, such as hydroxy, amino, and the like. Such protecting groups may be removed to provide the compounds (9) including free hydroxy, amino, and other like groups. It is appreciated that like conversions may be performed on the group $R^D$.

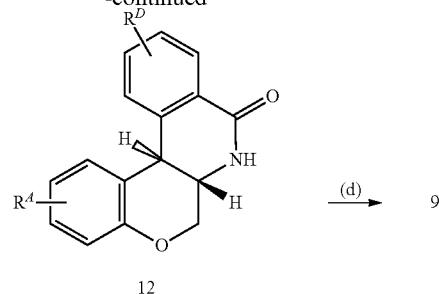

In another embodiment, the compounds and process shown in Scheme 4 are described. Chromenoisoquinolines (9) are converted to derivatives that include a chiral auxiliary, such as optically active amine derivatives (13), as illustrated in Scheme 4.

Scheme 4

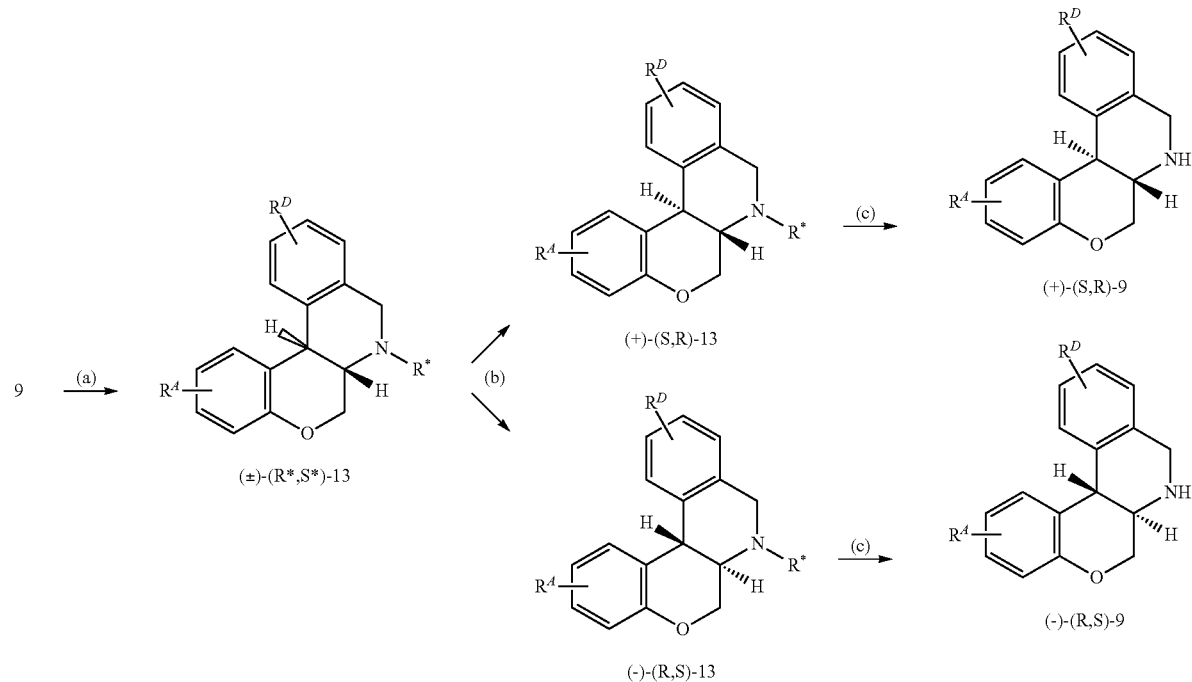

Such chiral auxiliaries may be used to provide a means of separating enantiomers by resolution, crystallization, chromatography, and the like. Illustratively, diastereomers (13) are separated to provide the substantially optically pure or optically pure ((R,S)-13). The chiral auxiliary on compound ((R,S)-13) is removed to provide substantially optically pure or optically pure ((R,S)-9).

In another embodiment, the compounds and process shown in Scheme 5 are described. Compounds (9), including optically variations thereof, are derivatized at the ring nitrogen with groups R[7], as described herein, to prepare compounds (14).

Scheme 5

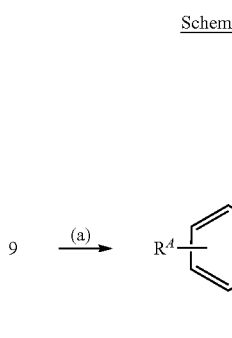

It is appreciated that the group R[7] may be introduced earlier in the syntheses as a routine optimization of the processes described herein, such as by the corresponding reaction of compounds (7), (8), (11), or (12) prior to the cyclization and/or reducing step.

It is to be understood that the reagents used to perform the chemical reactions and/or transformations shown in the foregoing schemes are illustrative. Alternative reagents for carrying out the synthetic steps described herein are also contemplated, including those described by Larock in "Comprehensive Organic Transformations, a guide to functional group preparations," VCH Publishers, Inc. New York (1989), the disclosure of which in its entirety is incorporated herein by reference.

EXAMPLES

The following Examples further illustrate embodiments and aspects of the invention described herein; however, such exemplary embodiments are understood to be illustrative, and are not intended to, nor should they be interpreted to limit the invention in any way. The Examples were prepared by the routes illustrated in Schemes 6, 7, 8, 9 and 10. Unless otherwise indicated, solvents were evaporated under reduced pressure.

Scheme 6

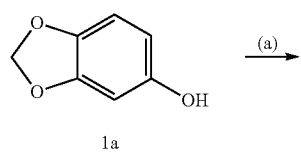

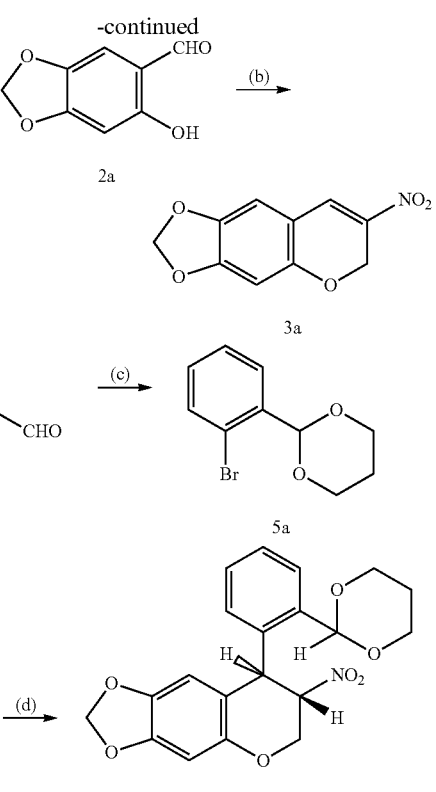

(a) Cl$_2$CHOMe, SnCl$_4$, CH$_2$Cl$_2$;
(b) 2-nitroethanol, dibutylamine, phthalic anhydride, PhMe, reflux;
(c) propanediol, p-toluenesulfonic acid;
(d) Mg, THF.

Example 1

6-Hydroxybenzo[1,3]dioxole-5-carbaldehyde (2a). Sesamol (1a) (16.95 g, 1.23 mol) was dissolved in 350 ml CH$_2$Cl$_2$ in a two necked round bottom flask connected to a condenser. SnCl$_4$ (35.4 ml, 3.07 mmol) was added and the solution was stirred at 0° C. Cl$_2$CHOCH$_3$ (11.7 ml, 1.29 mol) was added dropwise, and the solution was warmed to room temperature. The dark bluish mixture was cooled, and poured into a flask containing 500 ml of ice and water. The water layer was discarded, and the organic phase was filtered through Celite. The filtrates were washed with 2 M HCl (3×200 ml), and then with brine (1×100 ml). The solution was dried over MgSO$_4$, filtered, and the solvent evaporated. The dark brown solids were then dissolved in ethanol, stirred with charcoal and filtered through Celite. Solvent was evaporated and the product was recrystallized from methanol to give 7.74 g (38% yield): mp 119° C.

This Example was repeated on a larger scale. Sesamol (50.98 g, 369 mmol) was dissolved in 600 mL of CH$_2$Cl$_2$ followed by 52 mL (448 mmol) of SnCl$_4$ and the solution was cooled to 0° C. Cl$_2$CHOCH$_3$ (35 mL, 387.5 mmol) was added dropwise as the reaction mixture warmed to room temperature, and was then stirred for 3 h. The mixture was poured over ice, the water layer was separated and extracted once with CH$_2$Cl$_2$ (30 mL). The organic extracts were combined, washed with 2M HCl (5×100 mL), and brine (50 mL), and then passed through a small column packed with MgSO$_4$, which removed color. The solvent was evaporated to yield 28 g (46% yield): mp 119° C.; $^1$H-NMR (CDCl$_3$) δ 9.63 (s, 1, CHO); 6.87 (s, 1, ArH); 6.47 (s, 1, ArH); 6.02 (s, 2, ArOCH$_2$O); 1.54 (s, 1, ArOH); low resolution CIMS: m/z (rel. intensity) 167 (MH$^+$, 100). Anal. Calcd. for C$_8$H$_6$O$_4$: C, 57.84; H, 3.64. Found: C, 57.65; H, 3.76.

Example 2

6,7-Methylenedioxy-3-nitrochromene (3a). Aldehyde (2a) (6 g, 36.14 mmol) was dissolved in 300 ml of CH$_2$Cl$_2$ along with 3.1 ml of dibutylamine (18.16 mmol) and 10.72 g of phthalic anhydride in a two necked flask equipped with a Dean-Stark trap, a condenser and a dropping funnel. Nitroethanol (7 ml 97.69 mmol) was added dropwise over a period of 18 hours, while the solution was stirred at reflux. After addition, the reaction was stirred for an additional 24 hrs. The flask was then cooled to room temperature, filtered and the solution extracted with 2 M NaOH (300 ml×3) and brine (100 ml), then dried over MgSO$_4$. The solvent was then evaporated to leave a concentrated solution which was passed through a short column of silica to remove dark polar impurities. The isolated material was recrystallized from methanol to give 4.89 g (61% yield) of the title compounds as red needles: mp 139° C.; $^1$H-NMR (CDCl$_3$) δ 5.20 (s, 2, ArOCH$_2$), 6.02 (s, 2, OCH$_2$O), 6.49 (s, 1, ArH), 6.69 (s, 1, ArH), 7.75 (s, 1, ArCH).

Example 3

2-(2-Bromophenyl)-[1,3]dioxane (5a). ortho-Bromobenzaldehyde (4a) (8 g, 43.24 mmol) was stirred with 1,3 propanediol (4.7 ml, 64.86 mmol) and p-toluenesulfonic acid monohydrate (164 mg, 0.86 mmol) in benzene (150 ml) in a flask equipped with a Dean-Stark trap and a condenser. The mixture was heated at reflux for 12 hrs, cooled, and extracted with 2 M NaOH (100 ml), and brine (100 ml×3). The solution was dried over MgSO$_4$, and the solvent evaporated to the title compound in quantitative yield.

Example 4

6,7-Methylenedioxy-3-nitro-4-(2-[1,3]dioxan-2-yl-phenyl)-3,4-dihydro-(2H)-chromene (6a). Acetal (5a) (9.04 g, 37.22 mmol) was dissolved in 50 ml of dry THF under an inert atmosphere in a two necked flask equipped with a condenser. Magnesium (1.8 g, 74.44 mmol) and one drop of 1,2 dibromoethane were added. This mixture was stirred at 80° C. for 45 min, and cooled to room temperature. A 50 ml solution of 2.74 g of nitrochromene (3a) (12.41 mmol) in THF was cannulated into this flask. This mixture was stirred for 30 min, and water was added to quench the reaction. The mixture was extracted with CH$_2$Cl$_2$ (100 ml×3), the extracts washed with brine (100 ml), dried over MgSO$_4$ filtered, and the solvent evaporated to a brown oil from which (6a) precipitated spontaneously. The precipitate was filtered, rinsed with 30 ml of EtOAc and dried to give 2.91 g (61.4% yield). The remaining liquor was purified by flash column chromatography to give an additional 550 mg (72% combined yield): mp 207° C.; $^1$H-NMR (CDCl$_3$) δ 7.50 (m, 1, ArH); 7.29 (m, 2, ArH); 6.99 (m, 1, ArH); 6.47 (s, 1, ArH); 6.38 (s, 1, ArH); 5.90 (d, 2, ArOCH$_2$); 5.70 (s, 2, OCH$_2$O); 4.97 (s, 1, O$_2$CHAr); 4.71 (dq, 1, Ar$_2$CH, J=10 Hz); 4.23 (m, 2+1, CH$_2$(CH$_2$O)$_2$, CHNO$_2$); 3.98 (m, 2, CH$_2$(CH$_2$O)$_2$); 2.22 (m, 1, CH$_2$); 1.43 (d, 1, CH$_2$); Low resolution CIMS: m/z (rel. intensity) 386 (MH$^+$, 100). Anal. Calcd. for C$_{20}$H$_{19}$NO$_7$: C, 62.33; H, 4.97; N, 3.63. Found: C, 62.18; H, 5.37; N, 3.38.

Scheme 7

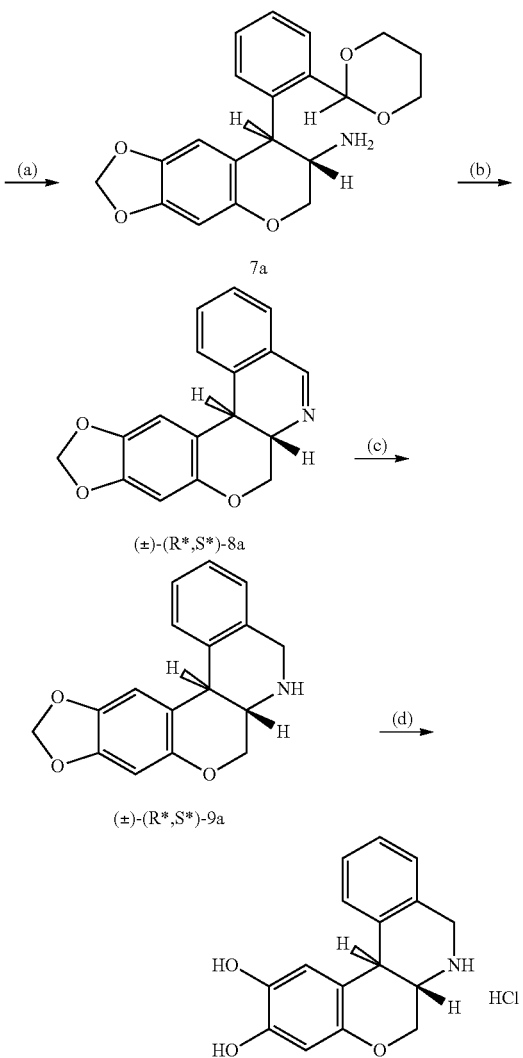

(a) Zn, acetic acid, heat;
(b) 1.2M HCl, 2.2M NaOH, sonication;
(c) NaCNBH$_4$, EtOH/THF;
(d) BCl$_3$.

Example 5

2,3-Methylenedioxy-6a,12b-dihydro-6H-chromeno[3,4-c]isoquinoline ((±)-(R*,S*)-8a). Acetal (6a) (3 g, 7.8 mmol) was dissolved in 150 ml THF and 50 ml of acetic acid. Zinc dust (2.5 g) was added through a powder funnel, and the mixture was stirred with a condenser at 70° C. for 3 hours. The mixture was cooled, filtered, rinsed with warm THF and the solvents evaporated to dryness. The resulting amine (7a) was dissolved in 50 ml of 2 M ethanolic HCl, and the solution was stirred at room temperature for 1 hr to give the unprotected aldehyde (not shown in Scheme 7). The solvents were evaporated and 100 ml of 2 M NaOH was added. The mixture was pulverized using a sonicator and stirred with 150 ml CH$_2$Cl$_2$ for 1 hr. The organic layer was removed, and the aqueous layer was extracted with CH$_2$Cl$_2$ (50 ml×3). The combined organic extracts were dried over MgSO$_4$ and evaporated. The resulting solids were recrystallized from ethanol to give 1.01 g (46% yield). $^1$H-NMR (CDCl$_3$) δ 3.65 (dt, 1, CHN, J=11 Hz), 4.0 (d, 1, ArCH J=11 Hz), 4.16 (t, 1, ArOCH$_2$), 4.8 (dd, 1, ArOCH$_2$), 6.0 (td, 1, ArOCH$_2$), 6.55 (s, 1, ArH), 6.97 (s, 1, ArH), 7.4-7.6 (m, 3, ArH), 7.74 (d, 1, ArH), 8.58 (s, 1, NCH).

This Example was repeated. Acetal 6a (1.84 g, 4.77 mmol) was dissolved in a mixture of 70 mL THF and 30 mL acetic acid. Zinc dust (1.9 g, 30 mmol) was added through a powder funnel and the mixture was stirred at 70° C. for 3 h at reflux. The mixture was cooled, filtered, and the solid metal and salts rinsed with warm THF. The filtrates were concentrated to dryness and the residue was dissolved in 50 mL of 2 M ethanolic HCl, and stirred at room temperature for 1 h to give the deprotected aldehyde. The solvents were evaporated and 100 mL of 2M NaOH were added. The mixture was stirred with 150 mL CH$_2$Cl$_2$ for 1 hr. The organic layer was recovered and the aqueous layer was extracted with CH$_2$Cl$_2$ (3×20 mL). The combined organic extracts were dried over MgSO$_4$ and concentrated to dryness. The residual solid was recrystallized from EtOH to yield 1.16 g (87%): mp 191° C.; $^1$H-NMR (CDCl$_3$): δ 3.67 (dt, 1, CHN, J=11 Hz); 3.98 (d, 1, ArCH J=11 Hz); 4.16 (t, 1, ArOCH$_2$); 4.8 (dd, 1, ArOCH$_2$); 6.0 (dd, 1, ArOCH$_2$O); 6.55 (s, 1, ArH); 6.97 (s, 1, ArH); 7.4-7.6 (m, 3, ArH); 7.74 (d, 1, ArH); 8.58 (s, 1, NCH); low resolution CIMS: m/z (rel. intensity), 280 (MH$^+$, 100). Anal. Calcd. for C$_{17}$H$_{13}$NO$_3$: C, 73.11; H, 4.69; N, 5.02. Found: C, 72.77; H, 4.62; N, 4.73.

Example 6

2,3-Methylenedioxy-6a,7,8,12b-tetrahydro-6H-chromeno [3,4-c]isoquinoline ((±)-(R*,S*)-9a). Imine ((±)—(R*,S*)-8a) (880 mg, 3.15 mmol) was dissolved in 250 ml of a 60:30 mixture of EtOH/THF. NaCNBH$_4$ (200 mg, 3.15 mmol) was added stirred until dissolved, followed by 1.6 ml of 2 M ethanolic HCl, and the mixture was stirred under an inert atmosphere for 4 hrs. The solution evaporated to one fourth of its volume and made basic with NaOH. Water was added and the mixture was extracted with CH$_2$Cl$_2$ (100 ml×3). The extracts were washed with brine, and the organic phase was dried over MgSO$_4$. The solvent was evaporated and the resulting solids recrystallized from ethanol to yield 570 mg (64% yield): mp 188° C.; $^1$H-NMR (CDCl$_3$) δ 3.11 (dt, 1, CHN, J=11.1 Hz), 4.02 (d, 1, ArCHAr, J=11.4 Hz), 4.10 (t, 1, ArOCH$_2$), 4.24 (s, 2, ArCH$_2$N), 4.47 (q, 1, ArOCH$_2$), 5.95 (s, 2, OCH$_2$O), 6.55 (s, 1, ArH), 6.92 (s, 1, ArH), 6.88 (s, 1, ArH), 7.35 (m, 4, ArH).

This Example was repeated. Imine ((±)—(R*,S*)-8a) (1.16 g, 4.15 mmol) was dissolved in 250 mL of 60:30 EtOH/ THF. NaCNBH$_4$ (261 mg; 4.15 mmol) was added with stirring until it dissolved. The mixture was acidified by addition of 2.1 mL of 2M ethanolic HCl and the reaction was stirred under an inert atmosphere for 4 h. The solution was evaporated to one-fourth its volume and made basic with NaOH. Water was added and the mixture was extracted with CH$_2$Cl$_2$ (3×50 mL). The extracts were washed with brine, and the organic layer was dried over MgSO$_4$. After filtration, the solvent was evaporated and the residual solid was recrystallized from ethanol to yield 0.922 g (79%): mp 188° C.; low resolution CIMS: m/z (rel. intensity) 282 (MH$^+$, 100); Anal. Calcd. for C$_{17}$H$_{15}$NO$_3$: C, 72.58; H, 5.37; N, 4.98. Found: C, 72.22; H, 5.42; N, 4.69.

Example 7

2,3-Dihydroxy-6a,7,8,12b-tetrahydro-6H-chromeno[3,4-c]isoquinoline hydrochloride ((±)—(R*,S*)-9b). Amine ((±)-(R*,S*)-9a) (570 mg, 2.03 mmol) was dissolved in 40 ml CH$_2$Cl$_2$ and the solution kept at −78° C. under an inert atmosphere. 1 M BCl$_3$ (8.1 ml) was added through a syringe and the solution was warmed to 0° C., and stirred for 4 hrs. Methanol (20 ml) was added to quench the boron reagent and the solution was stirred for another hour. The solvents were evaporated, the residue was redissolved in MeOH, and the solvents were evaporated again to the title compound (quantitative yield): 180° C. $^1$H-NMR (D$_2$O) δ 3.16 (dt, 1, CHN, J=11.1 Hz), 4.02 (t, 1, ArOCH$_2$), 4.14 (d, 1, ArCH, J=11:4 Hz), 4.35 (2d, 2, NCH$_2$Ar), 4.37 (m, 1, ArOCH$_2$), 6.42 (s, 1, ArH), 6.88 (s, 1, ArH), 7.28 (m, 4, ArH). The compound was recrystallized (MeOH) and dried in vacuo at 70° C.: low resolution ESIMS: m/z (relative intensity) 268 (M$^+$, 100).

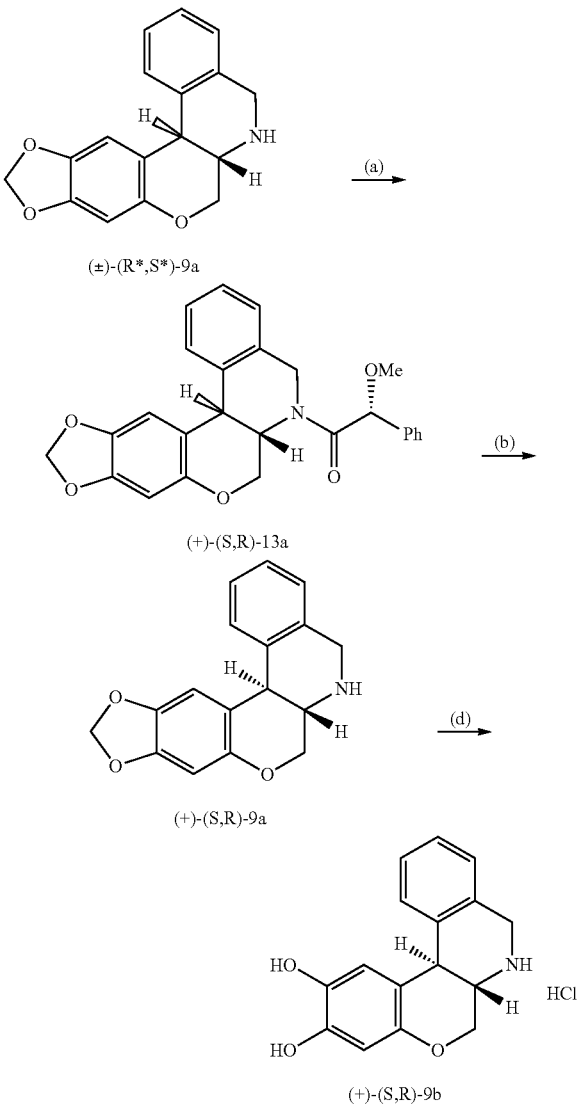

Scheme 8

(±)-(R*,S*)-9a (+)-(S,R)-13a (+)-(S,R)-9a (+)-(S,R)-9b (a) (R)-(-)-α-methoxyphenylacetyl chloride;
(b) LiEt$_3$BH;
(c) BCl$_3$.

Example 8

(2S)-1-(2,3-dioxolane-6,6a-dihydro-8H-chromeno[3,4-c] isoquinolin-7-(12bH)-yl)-2-methoxy-2-phenylethanone ((−)-(R,S)-13a & (+)-(S,R)-13a). R-(−)-α-Methoxyphenylacetic acid (714 mg, 4.30 mmol) was added to a round bottom flask containing 12 ml of $SOCl_2$, and the mixture was stirred under an inert atmosphere for 1 h at room temperature. The solvent was evaporated, resuspended in benzene, and evaporated again to give R-(−)-O-methylmandeloyl chloride. That residue was dissolved in 5 ml $CH_2Cl_2$ and added to a round-bottom flask containing 930 mg of Amine ((±)—(R*,S*)-9a) in 20 ml of $CH_2Cl_2$ and 10 ml 0.5M NaOH. That mixture was stirred for 6 hrs, and then the layers were separated. The aqueous layer was extracted with $CH_2Cl_2$ (30 ml) and the organic layer washed with water (30 ml×2) and brine (50 ml). The combined organic layers were dried over $MgSO_4$, filtered, and evaporated. The resulting residue was purified by column chromatography (2; 1 hexanes/EtOAc) to give (a) 616 mg (43%) of a faster moving component ((−)-(R,S)-13a): mp 170° C.; $[\alpha]_D$-125.0°; $^1$H NMR ($CDCl_3$) δ 7.45 (d, 1, ArH), 7.40-7.15 (m, 3, ArH); 6.97 (t, 2, ArH); 6.92 (s, 1, ArH); 6.51 (s, 1, ArH); 6.22 (d, 1, ArH); 5.93 (d, 2, $OCH_2O$); 5.13 (s, 1, OCH); 5.08 (m, 1, $OCH_2$); 4.40 (d, 1, $CH_2N$); 4.17 (m, 2, $Ar_2CH$, $OCH_2$); 3.76 (m, 1, CHN); 3.64 (s, 1, $OCH_3$); low resolution CIMS m/z (relative intensity) 430 ($MH^+$, 100); and (b) 661 mg (46%) of a slower moving component ((+)-(S,R)-13a): mp 186° C.; $[\alpha]_D$+197.20; $^1$H NMR ($CDCl_3$) δ 7.50 (d, 1, ArH), 7.48-7.30 (m, 3, ArH), 7.12 (t, 2, ArH), 6.95 (s, 1, ArH); 6.67 (d, 1, ArH); 6.52 (s, 1, ArH); 5.95 (d, 2, $ArOCH_2O$); 5.17 (m, 1, $ArOCH_2$); 5.07 (s, 1, ArCHO); 4.91 (d, 2, J=15 Hz); 4.20 (m, 1, $ArOCH_2$); 4.09 (d, 1, $Ar_2CH$, J=14 Hz); 3.78 (m, 1, CHN); 3.42 (s, 3, $OCH_3$); low resolution CIMS m/z (relative intensity) 430 ($MH^+$, 100).

Additional details for the optical resolution of the compounds described herein are described by Knoerzer; Nichols; Brewster; Watts; Mottola; Mailman in "Dopaminergic benzo[a]phenanthridines: resolution and pharmacological evaluation of the enantiomers of dihydrexidine, the full efficacy $D_1$ dopamine receptor agonist," *J. Med. Chem.* 37:2453-2460 (1994), the disclosure of which is incorporated herein by reference.

Example 9

(−)-(6aR,12bS)-2,3-Methylenedioxy-6a,7,8,12b-tetrahydro-6H-chromeno[3,4-c]isoquinoline hydrochloride ((−)-(R,S)-9a). Diastereomeric amide ((−)-(R,S)-13a) (615 mg, 1.433 mmol) was dissolved in 50 mL of dry THF and stirred at 0° C. under Argon. A 1 M solution of $LiEt_3BH$ (9 mL, 9 mmol) was added through a syringe, and the solution was stirred for 12 h at 0° C. The reaction mixture was poured into 15 mL of ice-cooled 2 M HCl, the aqueous layer was washed with ether (2×15 mL), and made basic with $NH_4OH$. The free amine was extracted from the aqueous suspension with $CH_2Cl_2$ (2×15 mL) and evaporated. The residue was purified by column chromatography over silica gel eluting with 1:1 hexanes/EtOAc to give 374 mg (93%): mp 163° C.; $^1$H NMR ($CDCl_3$) δ 7.48 (d, 1, ArH), 7.35-7.25 (m, 3, ArH); 6.91 (s, 1, ArH); 6.53 (s, 1, ArH); 5.95 (s, 2, $ArOCH_2O$); 4.47 (dd, 1, $ArOCH_2$, J=5.1 Hz, $J_{gem}$=10.2 Hz); 4.24 (s, 1, $ArCH_2N$); 4.09 (t, 1, $OCH_2$, J=11.4 Hz); 4.03 (d, 2, ArCHAr, J=11.4 Hz); 3.12 (dt, 1, NCH, $J_{gem}$=11.4 Hz, J=4.2 Hz); $[\alpha]_D$-35.3°; low resolution CIMS: m/z (relative intensity) 282 ($MH^+$, 100).

Example 10

(+)-(6aS,12bR)-2,3-Methylenedioxy-6a,7,8,12b-tetrahydro-6H-chromeno[3,4-c]isoquinoline hydrochloride ((+)-(S,R)-9a). The title compound was prepared from diastereomeric amide ((+)-(S,R)-13a) according to the procedure of Example 9 to give 589 mg: mp 163° C.; $^1$H NMR ($CDCl_3$) δ 7.48 (d, 1, ArH), 7.35-7.25 (m, 3, ArH); 6.91 (s, 1, ArH); 6.53 (s, 1, ArH); 5.95 (s, 2, $ArOCH_2O$); 4.47 (dd, 1, $ArOCH_2$, J=5.1 Hz, $J_{gem}$=10.2 Hz); 4.24 (s, 1, $ArCH_2N$); 4.09 (t, 1, $OCH_2$, J=11.4 Hz); 4.03 (d, 2, ArCHAr, J=11.4 Hz); 3.12 (dt, 1, NCH, $J_{gem}$=11.4 Hz, J=4.2 Hz); $[\alpha]_D$+35.3°.

Example 11

(−)-(6aR,12bS)-2,3-Dihydroxy-6a,7,8,12b-tetrahydro-6H-chromeno[3,4-c]isoquinoline hydrochloride ((−)-(R,S)-9b). Prepared according to the procedure described in Example 7 for ((±)—(R*,S*)-9b): mp 185-190° C. (dec.); $^1$H NMR ($D_2O$) δ 7.43-7.55 (m, 4, Ar); 7.07 (s, 1, ArH); 6.61 (s, 1, ArH); 4.60 (dd, 1, $ArOCH_2$); 4.55 (2d, 2, $ArCH_2N$, J=7 Hz); 4.34 (d, 1, ArCHAr, J=11.5 Hz); 4.20 (t, 1, $ArOCH_2$, J=10 Hz); 3.35 (dt, 1, NCH, $J_{trans}$=11.5 Hz, $J_2$=4.2 Hz); low resolution ESIMS: m/z (relative intensity) 268 ($M^+$, 100).

Example 12

(+)-(6aS,12bR)-2,3-Dihydroxy-6a,7,8,12b-tetrahydro-6H-chromeno[3,4-c]isoquinoline hydrochloride ((+)-(S,R)-9b). Prepared according to the procedure described in Example 7 for ((±)-(R*,S*)-9b): mp 185-195° C. (dec); $^1$H NMR ($D_2O$) δ 7.43-7.55 (m, 4, Ar); 7.07 (s, 1, ArH); 6.61 (s, 1, ArH); 4.60 (dd, 1, $ArOCH_2$); 4.55 (2d, 2, $ArCH_2N$, J=7 Hz); 4.34 (d, 1, ArCHAr, J=11.5 Hz); 4.20 (t, 1, $ArOCH_2$, J=10 Hz); 3.35 (dt, 1, NCH, $J_{trans}$=11.5 Hz, $J_2$=4.2 Hz); $[\alpha]_D$+35.3°; low resolution ESIMS: m/z (relative intensity) 268 ($M^+$, 100).

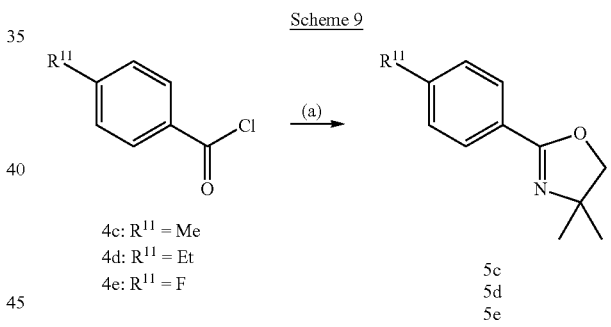

Scheme 9

-continued

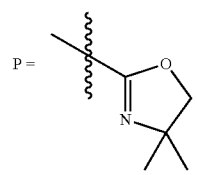

(a) H₂NC(CH₃)₂CH₂OH, SOCl₂;
(b) n-BuLi.

Example 13

4,4-Dimethyl-2-p-tolyl-2-oxazoline (5c). 2-Amino-2-methyl-propanol (14.5 ml, 151 mmol) was stirred in 30 ml CH₂Cl₂ at 0° C. 4-Methylbenzoyl chloride (p-toluoyl chloride) (4c) (11.69 g, 75.6 mmol) was added dropwise. 4-Methylbenzoyl chloride may be prepared by conventional processes. The mixture was stirred for 4 hrs, at which time 11 ml of SOCl₂ (151 mmol) was added slowly. The mixture was warmed to room temperature overnight. Water (30 ml) was added, the layers separated, and the organic layer washed with water (5×20 ml). The combined water layer was rinsed once with 15 ml CH₂Cl₂, and then basified with aqueous ammonia. The cloudy mixture was extracted with CH₂Cl₂ (3×30 ml), dried over MgSO₄, filtered and the solvent evaporated to yield 10.7 g as a white crystalline solid (75% yield).

Example 14

4,4-dimethyl-2-(4-methyl-2-(7-nitro-6H-[1,3]methylenedioxy[4,5-g]chroman-8-yl)phenyl)-oxazoline (6c). The toluoyl oxazoline (5c) was dissolved in 40 ml of dry THF, and stirred at −45° C. (CO₂/PhCl). n-BuLi in hexanes (8.14 ml of a 2.5 M solution) was added slowly to turn the solution bright orange. The solution was stirred for 1 hr and then cannulated into a flask containing 3 g (13.6 mmol) of the nitro chromene (3a) dissolved in 200 ml of dry THF at −78° C. The mixture was warmed to room temperature over one hour, and quenched with an aqueous solution of saturated NH₄Cl. The mixture was extracted with CH₂Cl₂ (4×30 ml), and the organic extracts rinsed with water (50 ml), then brine (20 ml). The extracts were dried over MgSO₄, filtered and the solvent evaporated to a dark oil, which was dissolved in 40 ml of MeOH to induce immediate crystallization. The solution was cooled to 0° C. overnight, and the crystals filtered and rinsed with cold methanol to yield 3.27 g as cream-colored crystals. A second crop was obtained by evaporation of the solvent, addition of MeOH and cooling to obtain a total of 3.52 g (65.5% yield); mp 167° C. (67% yield): ¹H-NMR (CDCl₃): δ 7.85 (d, 1H, ArH); 7.14 (d, 1H, ArH); 6.79 (s, 1H, ArH); 6.45 (s, 1H, ArH); 6.32 (s, 1H, ArH); 5.92-5.86 (m, 2H, OCH₂); 4.21 (br, 1H, ArCHAr); 4.93 (br, 1H, CHNO₂); 4.65-4.59 (m, 1H, OCH₂); 4.15-4.11 (dd, 1H, $J_{gem}$=11.7 Hz, $J_{vic}$=2.4 Hz); 4.06 (s, 2H, oxazoline CH₂); 2.28 (s, 3H, CH₃); 1.32-1.3 (2s, 6H, 2CH₃). CIMS: m/z (relative intensity) 411 (M+H⁺, 100).

Scheme 10

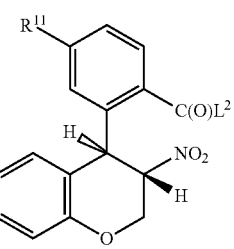

6c
6d
6e

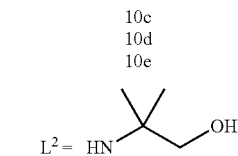

10c
10d
10e

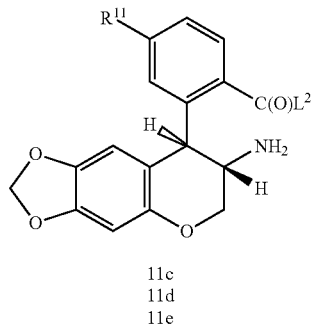

11c
11d
11e

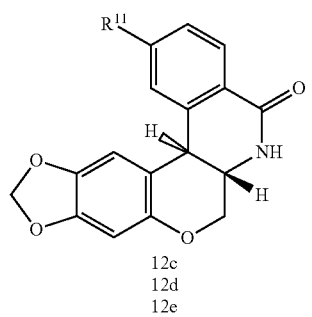

12c
12d
12e

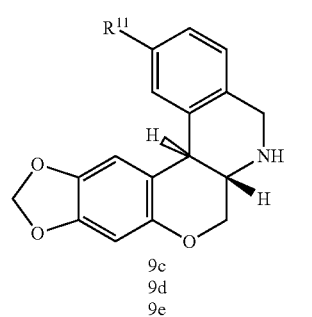

9c
9d
9e

-continued

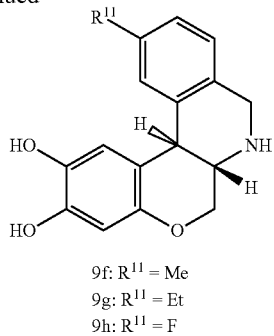

9f: R[11] = Me
9g: R[11] = Et
9h: R[11] = F (a) HCl, THF, H$_2$O;
(b) Zn, acetic acid;
(c) NH$_4$OH;
(d) 1. BH$_3$—THF, 2. HCl, EtOH, 3. NH$_4$OH;
(e) BBr$_3$, CH$_2$Cl$_2$.

Example 15

N-(1-hydroxy-2-methylpropan-2-yl) 4-methyl-2-(7-nitro-6H-2,3-methylenedioxychroman-8-yl)benzamide (10c). Compound (6c) was dissolved in 60 ml THF and 20 ml of a 2 M aqueous HCl solution was added. The solution was stirred for 48 hrs, then the total volume was reduced to one half under reduced pressure. The mixture was extracted with EtOAc (3×30 ml), and the combined organic layer was washed with water (30 ml), dried over MgSO$_4$, filtered and the solvent removed evaporated to yield 940 mg as a tan solid (90% yield).

Example 16

2,3-methylenedioxy-11-methyl-6a,7-dihydro-6H-12bH-chromeno[3,4-c]isoquinolin-8-one ((±)—(R*,S*)-12c). Zn powder (5 g) was added to compound (10c) (2.9 g) dissolved in 50 ml CH$_3$COOH. The mixture was stirred under inert atmosphere for 3 hrs, then filtered through Celite. The filter cake containing amine (11c) was rinsed with water, and the combined aqueous layer was then basified to pH 9 by slow addition of aqueous ammonia to obtain a white precipitate. To this solution, 30 ml of MeOH was added, the mixture was stirred, and the resulting crystals contents were filtered, and rinsed with cold MeOH to yield 1.45 g as pure white crystals (67% yield). MP: >250° C. $^1$H-NMR (CDCl$_3$): δ 7.98 (d, 1H, ArH); 7.46 (s, 1H, ArH); 6.99 (s, 1H, ArH); 6.51 (s, 1H, NH); 6.00-5.96 (2d, 2H, OCH$_2$O); 4.30-4.26 (dd, 1H, OCH$_2$, $J_{gem}$=9.1 Hz, $J_{vic}$=3.6 Hz); 4.21 (d, 1H, ArCHAr, $J_{trans}$=11.1 Hz); 3.95 (t, 1H, OCH$_2$, $J_{gem}$=9.1 Hz); 3.89-3.86 (dd, 1H, CHN, $J_{trans}$=11.1 Hz, $J_{vic}$=3.6 Hz); 2.41 (s, 3H, CH$_3$). EIMS: m/z (relative intensity) 309 (M$^+$, 100).

Example 17

11-Methyl-2,3-methylenedioxy-6a,7,8,12b-tetrahyhydro-6H-chromeno[3,4-c]isoquinoline ((±)—(R*,S*)-9c). Compound (12c) (1.3 g, 4.28 mmol) was stirred in 200 ml of dry THF at reflux. Into this flask, 21.4 ml of a 1 M BH$_3$-THF in THF was added and the solution stirred at reflux for 30 hrs. The solution was cooled to 0° C. and water added to quench the reagent. The solution was reduced to one third of its original volume, then the volume was doubled by addition of H$_2$O. The mixture was extracted with EtOAc, dried over MgSO$_4$, filtered and the solvent removed under reduced pressure to obtain a solid which was dissolved in 30 ml of a 2 M solution of HCl in ethanol. This solution was stirred at 70° C. for 40 minutes and then cooled over 4 hrs to obtain crystals which were filtered to obtain 1.06 g as the HCl salt. The liquor was reduced to one sixth of its volume to obtain 0.13 g as a second batch. This combined salt was suspended in MeOH, and ammonia was added to pH 9. Water was added and the suspension was extracted in CH$_2$Cl$_2$, dried over MgSO$_4$, filtered, and the solvent evaporated to 1.05 g (85% yield), which may be recrystallized from MeOH, if desired. MP: 97-99° C. $^1$H-NMR (MeOD): δ 7.26-7.23 (m, 2H, 2ArH); 7.16-7.13 (d, 1H, ArH); 6.86 (s, 1H, ArH); 6.48 (s, 1H, ArH); 5.91-5.88 (2d, 2H, OCH$_2$O); 4.46-4.39 (m, 3H, OCH$_2$, CH$_2$N); 4.22 (d, 1H, ArHAr, $J_{trans}$=11.4 Hz); 4.03 (t 1H, OCH$_2$, $J_{gem}$=10.5 Hz); 2.30 (s, 3H, CH$_3$). EIMS: m/z (relative intensity) 295 (M$^+$, 100).

Example 18A

11-Methyl-2,3-dihydroxy-6a,7,8,12b-tetrahydro-6H-chromeno[3,4-c]isoquinoline hydrobromide ((±)—(R*,S*)-9f). BBr$_3$ (8.1 ml of a 1 M solution) was added through a syringe to a solution of compound ((±)—(R*,S*)-9c) (300 mg, 1.016 mmol) in 15 ml CH$_2$Cl$_2$ at −78° C. under an inert atmosphere. The solution was warmed to 0° C., and stirred for 4 hrs. Methanol (50 ml) was added to quench the reagent and the solution was stirred for another hour. The solvent was evaporated and the residue was dissolved in 50 ml of methanol. The solvent was evaporated to a yellow film, which was dissolved in 0.5 ml of isopropanol, and stored at −15° C. until the appearance of crystals (ca. 2 months). The solvent was evaporated, and the residue was triturated with cold EtOH and filtered. MP: 195-200° C. dec. $^1$H-NMR (D$_2$O): δ 7.30 (d, 1H, ArH); 7.28 (s, 1H, ArH); 7.22 (d, 1H, ArH); 6.99 (s, 1H, ArH); 6.52 (s, 1H, ArH); 4.56-4.51 (dd, 1H, OCH$_2$, $J_{gem}$=10.2 Hz, $J_{vic}$=4.5 Hz); 4.51-4.42 (2d, 2H, CH$_2$N); 4.22 (d, 1H, ArCHAr, $J_{trans}$=11.7 Hz); 4.13 (t, 1H, OCH$_2$); 3.24 (dt, 1H, CHN, $J_{trans}$=11.7 Hz, $J_{vic}$=4.5 Hz). ESIMS: m/z (relative intensity) 283 (M$^+$, 100).

Example 18B

11-Ethyl-2,3-dihydroxy-6a,7,8,12b-tetrahydro-6H-chromeno[3,4-c]isoquinoline hydrobromide ((±)—(R*,S*)-9g). Prepared according to the synthesis of Examples 13-18A, except that 4-methylbenzoyl chloride was replaced with 4-ethylbenzoyl chloride.

Example 18C

11-Fluoro-2,3-dihydroxy-6a,7,8,12b-tetrahydro-6H-chromeno[3,4-c]isoquinoline hydrobromide ((±)-(R*,S*)-9h). Prepared according to the synthesis of Examples 13-18A, except that 4-methylbenzoyl chloride was replaced with 4-fluorobenzoyl chloride.

Example 18C

11-Trifluoromethyl-2,3-dihydroxy-6a,7,8,12b-tetrahydro-6H-chromeno[3,4-c]isoquinoline hydrobromide ((±)—(R*,S*) (not shown)). Prepared according to the synthesis of Examples 13-18A, except that 4-methylbenzoyl chloride was replaced with 4-(trifluoromethyl)-benzoyl chloride.

Example 19A (6aR,12bS)-11-Methyl-2,3-dihydroxy-6a,7,8,12b-tetrahydro-6H-chromeno[3,4-c]isoquinoline hydrobromide ((±)-(S,R)-9f). Prepared according to the synthesis of Examples 8, 9, and 18A, except that ((±)—(R*,S*)-9a) was replaced with ((±)—(R*,S*)-9c) to yield 221 mg (60% yield); mp 185-195° C.; [α]$_D$+35.3°; $^1$H-NMR (D$_2$O spectrum of the HCl salt) δ 7.43-7.55 (m, 4, Ar); 7.07 (s, 1, ArH); 6.61 (s, 1, ArH); 4.60 (dd, 1, ArOCH$_2$); 4.55 (2d, ABq, 2, ArCH$_2$N, J=7 Hz); 4.34 (d, 1, ArCHAr, J=11.5 Hz); 4.20 (t, 1, ArOCH$_2$, J=10 Hz); 3.35 (dt, 1, NCH, J$_{trans}$=11.5 Hz, J$_2$=4.2 Hz); ESIMS (low resolution) m/z (relative intensity) 268 (M$^+$, 100).

Example 19B (6aR,12bS)-11-Ethyl-2,3-Dihydroxy-6a,7,8,12b-tetrahydro-6H-chromeno[3,4-c]isoquinoline hydrobromide ((±)-(S,R)-9g). Prepared according to the synthesis of Examples 8, 9, and 18A, except that ((±)-(R*,S*)-9a) was replaced with ((±)-(S,R)-9).

Example 19C (6aR,12bS)-11-Fluoro-2,3-Dihydroxy-6a,7,8,12b-tetrahydro-6H-chromeno[3,4-c]isoquinoline hydrobromide ((+)-(S,R)-9h). Prepared according to the synthesis of Examples 8, 9, and 18A, except that ((±)—(R*,S*)-9a) was replaced with ((+)-(S,R)-9e).

Example 20

N-Allyl-2,3-methylenedioxy-6a,7,8,12b-tetrahydro-6H-chromeno[3,4-c]isoquinoline ((±)-(R*,S*)-9i). Prepared by alkylation of amine ((±)—(R*,S*)-9a) with allyl bromide and potassium carbonate in acetone. Additional details for the alkylation of the compounds described herein are described in U.S. Pat. No. 6,413,977, the disclosure of which is incorporated herein by reference.

Example 21

N-Propyl-2,3-methylenedioxy-6a,7,8,12b-tetrahydro-6H-chromeno[3,4-c]isoquinoline ((±)—(R*,S*)-9j). Prepared by reduction of allyl amine ((±)-(R*,S*)-9i) with palladium on charcoal in ethanol under a hydrogen atmosphere. Additional details for the reduction of the compounds described herein are described in U.S. Pat. No. 6,413,977, the disclosure of which is incorporated herein by reference.

Example 22

(±)-Trans-4,4-dimethyl-2-(3-(7-nitro-7,8-dihydro-6H-[1,3]dioxolo[4,5-g]chromen-8-yl)thiophen-2-yl)-4,5-dihydrooxazole (24)(Scheme 11). In a 500 ml flask and under a dry atmosphere, 4.71 g of 2-(2-thienyl)-4,4-dimethyloxazoline (30.737 mmol) were dissolved in 73 ml of dry Et$_2$O. This solution was cooled to −78° C. and 12.3 ml of a 2.5 M solution of nBuLi in hexanes were introduced dropwise. The solution was stirred for 15 min, then put in an ice/water bath and stirred for 30 min. The solution was then cooled again to −78° C. and a previously cooled (−78° C.) solution of 4 g of nitro-chromene 3 (18.083 mmol) in 150 ml of dry THF was introduced through a cannula. This mixture was allowed to warm to room temperature over one hour, and then quenched with an aqueous solution of saturated NH$_4$Cl. The mixture was extracted with CH$_2$Cl$_2$ (30 ml×4), and the organic extracts rinsed with water (50 ml) and then brine (20 ml). The extracts were dried over MgSO$_4$, filtered and the solvent removed under reduced pressure to yield a dark oil. This oil was dissolved in 40 ml of MeOH to induce crystallization of the product. The solution was then cooled to 0° C. overnight, the crystals filtered and then rinsed with cold methanol to yield 4.22 g of product as brown crystals. (59% yield). MP: 138-140° C. $^1$H-NMR (CDCl$_3$): δ 7.29 (d, 1H, thiophenyl H); 6.63 (d, 1H, thiophenyl H); 6.43 (s, 2H, 2ArH); 5.89 (2d, 2H, OCH$_2$O); 5.28 (br, 1H, ArCH); 4.99 (m, 1H, CHNO$_2$); 4.68-4.63 (m, 1H, OCH$_2$); 4.08-4.04 (m, 3H, OCH$_2$, oxazolinyl CH$_2$); 1.31-1.29 (2s, 6H, 2CH$_3$). EIMS: m/z (relative intensity) 411 (M+H$^+$, 100).

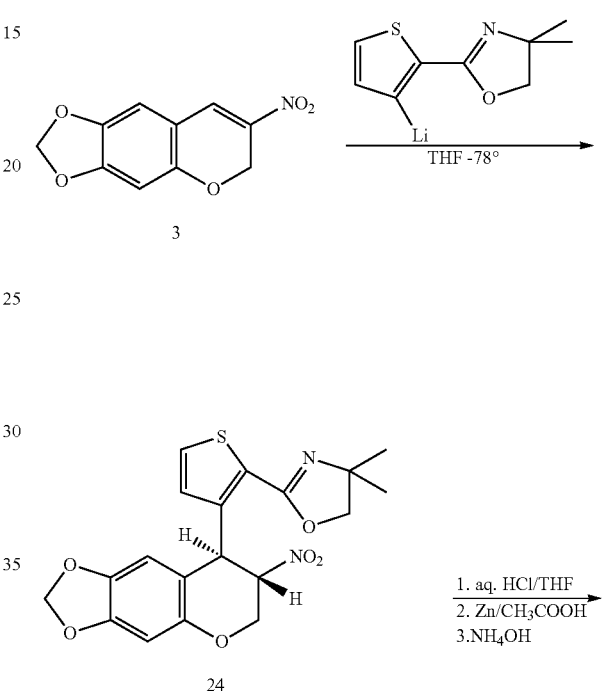

Example 23

(±)-Trans-9,10-methylenedioxy-5,5a,6,11b-tetrahydro-4H-chromeno[3,4-b]thieno[3,2-d]pyridin-4-one (25). In a 250 ml flask, 4.069 g of the nitro-oxazoline 24 was dissolved in 60 ml THF and 60 ml of a 2M aqueous HCl solution was added. This solution was stirred for 1 hrs at reflux, at which point the total volume was reduced to one half under reduced pressure. The mixture was then neutralized with 2 M NaOH, extracted with $CH_2Cl_2$ (30 ml×3), washed with water (30 ml), dried over $MgSO_4$, filtered and the solvents removed under reduced pressure to yield 940 mg of the HCl salt as a tan solid. This salt was dissolved in 50 ml $CH_3COOH$ and 5 g of zinc powder were added. The suspension was stirred under an inert atmosphere for 3 hrs. The mixture was then filtered, and the filtrates rinsed with $CH_3COOH$. The solvent was then removed by rotary evaporation and the remaining residue was dissolved in 30 ml EtOH and basified with ammonia to yield crystals. Cooling and filtration of this mixture yielded 240 mg of pure white crystals. MP: >250° C. $^1$H-NMR (DMSO-$d_6$): δ 8.32 (s, 1H, NH); 7.89 (d, 1H, thiophenyl H); 7.55 (d, 1H, thiophenyl H); 7.29 (s, 1H, ArH); 6.54 (s, 1H, ArH); 4.33-4.29 (dd, 1H, $OCH_2$, $J_{gem}$=9.9 Hz, $J_{vic}$=3.6 Hz); 4.23 (d, 1H, ArCH, $J_{trans}$=12.6 Hz); 3.99 (t, 1H, $OCH_2$, $J_{gem}$=10.5 Hz); 3.86-3.77 (m, 1H, CHN); 2.41 (s, 3H, $CH_3$). EIMS: m/z (relative intensity) 302 (M+H$^+$, 100).

Example 24

(+)-(6aS,12bR)-2,3-Dihydroxy-6a,7,8,12b-tetrahydro-6H-chromeno[3,4-c]isoquinoline hydrochloride ((+)-(S,R)-9b; Example 12)(+)-ODHX) is a potent agonist at the dopamine $D_1$ receptor. The abilities of the enantiomers of doxanthrine (ODHX) to stimulate cyclic AMP accumulation were initially examined using a heterologous expression system in HEK cells stably expressing the human dopamine $D_1$ receptor. Both enantiomers stimulated cyclic AMP accumulation in HEK-$D_1$ cells incubated with increasing concentrations of dopamine, (+)-ODHX, or (−)-ODHX for 15 min at 37° C. The (+)-ODHX displayed full intrinsic activity (109±6%) relative to dopamine, with an EC50 of ca. 50 nM (Table 1, FIG. 1).

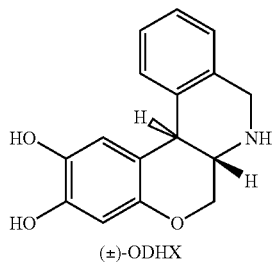

(±)-ODHX

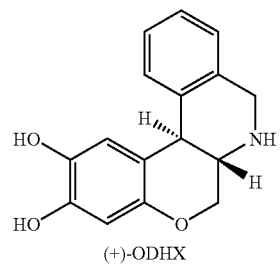

(+)-ODHX

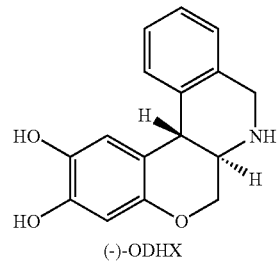

(−)-ODHX

The (−) enantiomer of doxanthrine ((−)-ODHX; (−)-(S,R)-9b, Example 11) displayed reduced potency and intrinsic activity when compared either to (+)-ODHX or to dopamine (FIG. 1, Table 1). The data presented in FIG. 1 have been normalized to the maximal cyclic AMP accumulation observed in the presence of dopamine. Data shown are the mean±SEM of six independent experiments assayed in duplicate.

TABLE 1

| | Potency (nM) and Intrinsic Activity at Dopamine $D_1$ and $α_{2C}$ Adrenergic Receptors | | | | | |
|---|---|---|---|---|---|---|
| | Cloned h$D_1$ | | Endogenous h$D_1$ | | $α_{2C}$ Adrenergic | |
| Ligand | EC50 (nM) | Intrinsic Activity (% dopamine) | EC50 (nM) | Intrinsic Activity (% dopamine) | EC50 (nM) | Intrinsic Activity (% forskolin) |
| Dopamine | 140 ± 44 | 100 ± 2 | 1230 ± 190 | 96 ± 3 | ND | ND |
| (±)-ODHX | ND | ND | 120 ± 30 | 80 ± 3 | ND | ND |
| (+)-ODHX | 53 ± 13 | 109 ± 6 | 190 ± 22 | 131 ± 13 | 151 ± 25 | 34 ± 7 |
| (−)-ODHX | 931 ± 99 | 85 ± 6 | 2860 ± 1990 | 32 ± 9 | 4.4 ± 2.3 | 69 ± 2 |
| Clonidine | NA | NA | NA | NA | 17 ± 3.2 | 61 ± 5 |

Figure 2A:
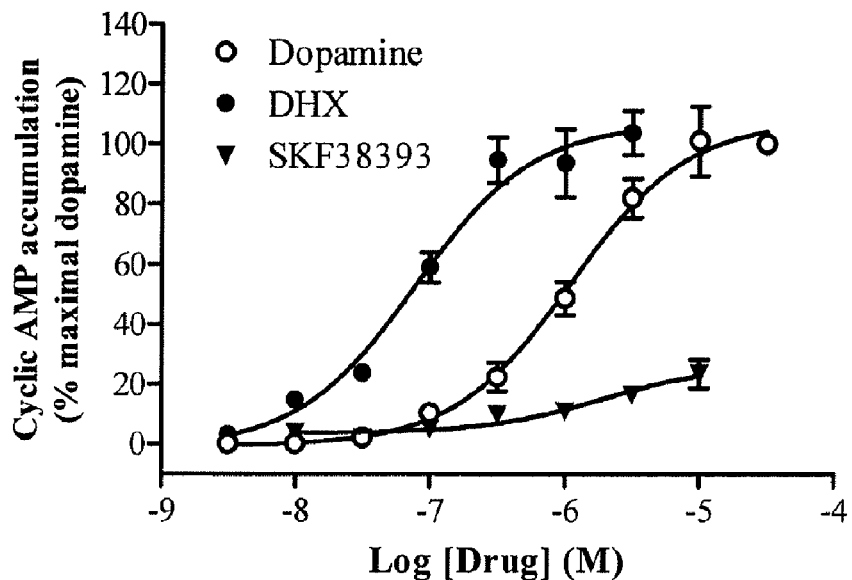
FIG. 2A is a graph showing cyclic AMP accumulation as a characterization of a human $D_1$-like dopamine receptor in MCF7 cells.
Figure 2B:
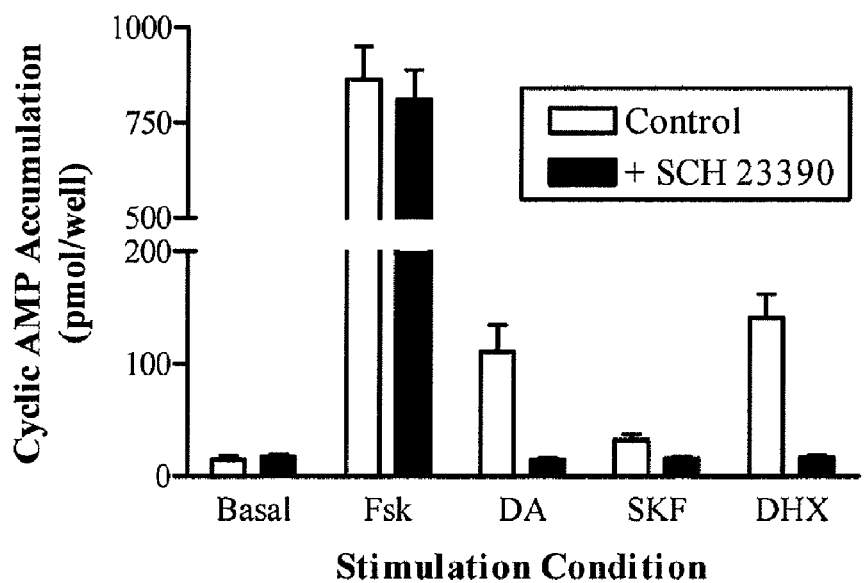
FIG. 2B is a bar graph showing the effect of added compounds on cyclic AMP accumulation in MCF7 cells.

Realizing that the functional activity of $D_1$ receptor agonists can be distorted in the presence of spare receptors in heterologous systems (Watts, V. J. et al., (1995) Synapse (New York, N.Y. 21, 177-187) prompted additional experiments in cells expressing an endogenous human $D_1$-like dopamine receptor that should give responses more similar to those that might occur in native tissues. For these studies cell growth studies implicating the presence of a $D_1$-like receptor in the breast cancer cell model, MCF7 cells (Johnson et al., (1995) Anticancer Drugs 6:471-474) were taken advantage of. To initiate these studies, an initial characterization of the human dopamine $D_1$-like receptor was initially characterized using a well-studied full $D_1$ receptor agonist, dihydrexidine (DHX; Brewster et al., (1990) J. Med. Chem. 33:1756-1764), and partial $D_1$ receptor agonist, SKF38393. MCF7 cells were incubated with increasing concentrations of dopamine, DHX, or SKF38393 for 15 min at 37° C. The data presented in FIG. 2A have been normalized to the maximal cyclic AMP accumulation observed in the presence of dopamine and are the mean±SEM of three or four independent experiments assayed in duplicate. The acute studies revealed that dopamine, DHX, and SKF38393 stimulated cyclic AMP accumulation in a dose-dependent manner in MCF7 cells, with EC50 values of 1120±100 nM, 81±1 nM, and 1060±290 nM, respectively (n=3). DHX was a "full" agonist relative to dopamine, whereas the selective partial agonist SKF38393 displayed reduced intrinsic activity (ca. 30% relative to dopamine) as expected (FIG. 2A). The intrinsic activity of DHX and SKF38393 in the MCF7 cells is consistent with previous studies using striatal tissue from humans (Gilmore et al., (1995) Neuropharmacology 34:481-488). To further characterize this cell model, antagonist studies using the dopamine $D_1$ antagonist, SCH23390 were carried out where cyclic AMP accumulation under basal conditions or following incubation with forskolin (FSK), dopamine (DA), DHX, or SKF38393 (SKF) in the absence (control) or presence of 1 μM of the $D_1$ dopamine receptor antagonist, SCH23390 was monitored. The data presented in FIG. 2B are the mean±SEM of three independent experiments assayed in duplicate. The results of these experiments revealed that incubation with SCH23390 resulted in a complete blockade of agonist-stimulated cyclic AMP accumulation. In contrast, SCH23390 failed to alter cyclic AMP accumulation under basal conditions or in response to forskolin, a direct activator of adenylate cyclase (FIG. 2B). These observations provide direct support for the presence of functional human dopamine $D_1$-like receptor in MCF7 cells.

Having established MCF7 cells as a model for assessing agonist activity in human $D_1$ dopamine receptors, the functional properties of the enantiomers of doxanthrine were then evaluated. MCF7 cells were incubated with increasing concentrations of dopamine, (±)-ODHX, (+)-ODHX, or (−)-ODHX for 15 min at 37° C. The data presented in FIG. 3A have been normalized to the maximal cyclic AMP accumulation observed in the presence of dopamine. Studies with racemic (±)-ODHX revealed that it was more potent than dopamine; however, its intrinsic activity appeared to be slightly reduced compared to dopamine (FIG. 3A and Table 1). Consistent with the results from the heterologous expression system, (+)-ODHX displayed full intrinsic activity and was capable of stimulating cyclic AMP accumulation to levels greater than those stimulated by dopamine, indicating that (+)-ODHX may have greater efficacy than dopamine. By contrast, (−)-ODHX was capable of stimulating cyclic AMP accumulation only to about 30% of that produced by dopamine. This finding suggests that (−)-ODHX is a weak partial agonist and may have potential antagonist activity at dopamine $D_1$ receptors (FIG. 3A, Table 1).

Thus, the ability of (−)-ODHX to antagonize both dopamine- and (+)-ODHX-stimulated cyclic AMP accumulation in MCF7 cells was evaluated. These studies were executed by completing drug dose-response curves in the absence or presence of 10 μM (−)-ODHX. These experiments revealed that 10 μM (−)-ODHX alone resulted in a significant increase in cyclic AMP levels. As anticipated, however, the addition of 10 μM (−)-ODHX reduced the intrinsic activity and potency of both dopamine and (+)-ODHX (FIGS. 3B-C, Table 1). The data presented in FIGS. 3B-C are the mean±SEM of three independent experiments assayed in duplicate.

Figure 4:
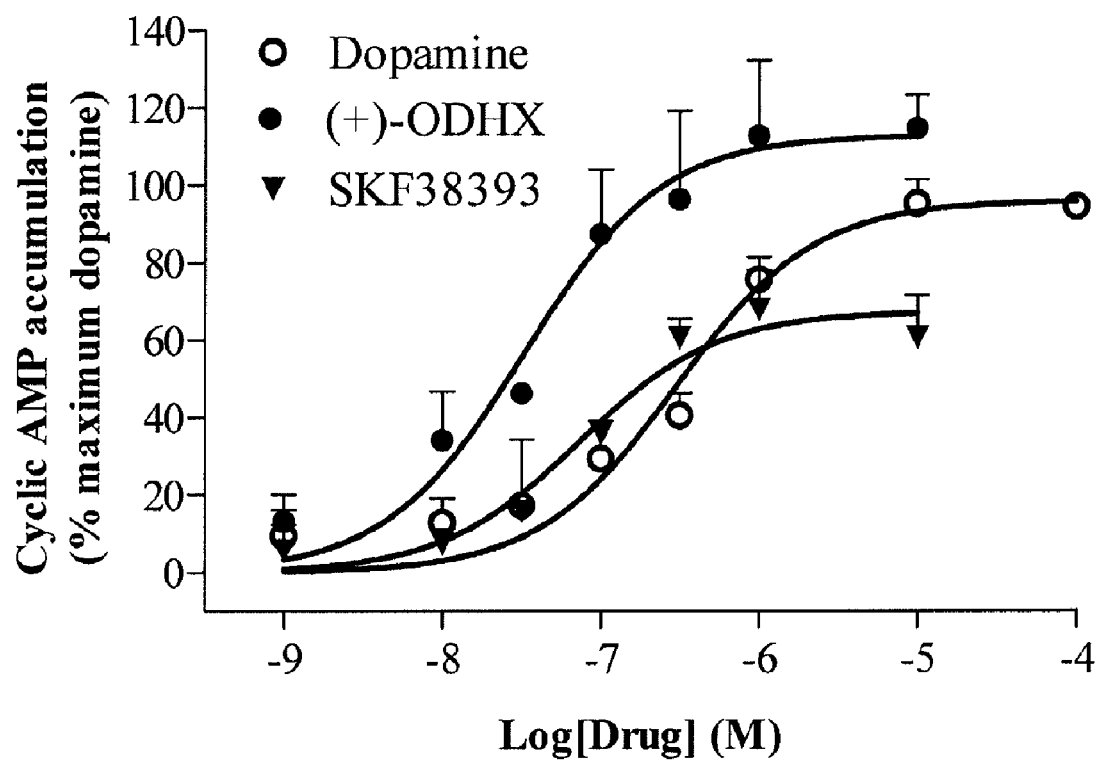
FIG. 4 is a graph showing the dose-dependent stimulation of cyclic AMP in porcine striatal homogenate.

The (−)-ODHX-induced reduction in the intrinsic activity of (+)-ODHX indicates the presence of significant antagonist activity in racemic (±)-ODHX. In lieu of access to native human striatal tissues to study action at the $D_1$-like dopamine receptor, (+)-ODHX was evaluated and compared to both dopamine and SKF38393 at native $D_1$-like dopamine receptors in porcine striatal tissue. Striatal tissue was incubated in the presence of increasing concentrations of dopamine, (+)-ODHX, or SKF38393 for 15 min at 30° C. This series of functional studies revealed that (+)-ODHX had high intrinsic activity (115±15%; n=3) and an EC50 of 68±14 nM; n=3 (see FIG. 4). Consistent with the data from the heterologous expression system, as well as the MCF7 cells, (+)-ODHX also was more potent than dopamine, which had an EC50 of 370±77 nM (n=3) in the porcine striatal tissue.

Example 25

Figure 5:
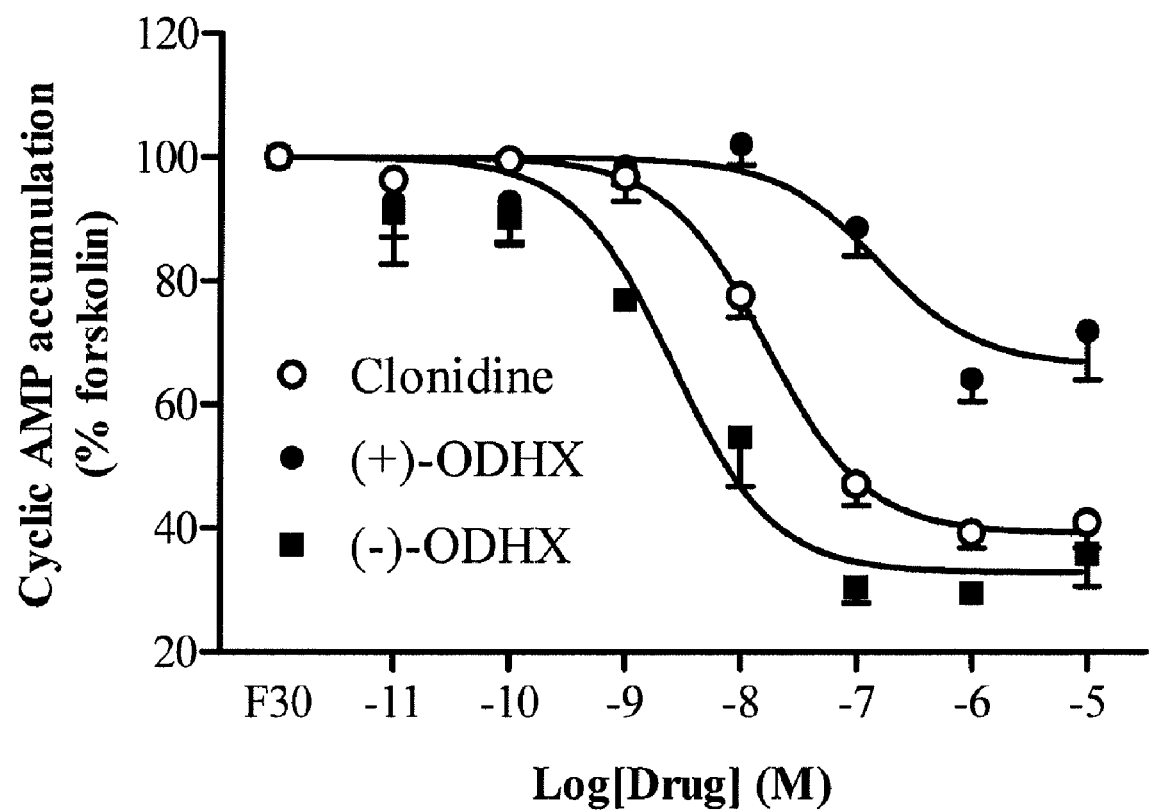
FIG. 5 is a graph showing the dose-response curves for $\alpha_{2C}$ receptor-mediated inhibition of forskolin-stimulated cyclic AMP accumulation.

(−)-ODHX is a potent agonist at the $\alpha_{2C}$-adrenergic receptor. Racemic doxanthrine ((±)-ODHX) was screened by the NIMH-sponsored Psychoactive Drug Screening Program, which demonstrated that it had significant affinity for the $\alpha_{2C}$ adrenergic receptor (ca. 2 nM). In light of this observation, the functional activity of the enantiomers of doxanthrine at $\alpha_{2C}$-adrenergic receptors was evaluated. A heterologous expression system in which HEK293 cells stably expressed the $\alpha_{2C}$ receptor was constructed to examine the ability of (+)-OHDX and (−)-ODHX to inhibit forskolin-stimulated cyclic AMP accumulation. HEK-$\alpha_{2C}$ cells were incubated with 30 μM forskolin in the presence of increasing concentrations of clonidine, (+)-ODHX, or (−)-ODHX for 15 min at 37° C. The prototypical potent $\alpha_2$ agonist, clonidine was used for comparison. Surprisingly, (−)-ODHX was nearly four-fold more potent than clonidine and more than 30-fold more potent than (+)-ODHX, with an EC50 of 4.4 nM±2.3; n=3 (FIG. 5, Table 1). The data presented have been normalized to the maximal cyclic AMP accumulation observed in the presence of forskolin alone and are the mean±SEM of three independent experiments assayed in duplicate. Perhaps even more striking was the marked difference in intrinsic activity between the two enantiomers at the $\alpha_{2C}$ receptor. The intrinsic activity of (−)-ODHX was equal to or greater than that of clonidine, whereas (+)-ODHX has only very weak intrinsic activity (i.e. 34±6% inhibition) that was ca. 50% of the intrinsic activity of (−)-ODHX. These data are consistent with the screening results from the NIMH-sponsored affinity studies of racemic (+)-ODHX, with the high affinity for $\alpha_{2C}$ adrenergic receptors reflecting the binding properties of (−)-ODHX. Additionally, the reversed stereoselectivity between dopamine $D_1$ and $\alpha_{2C}$ adrenergic receptors for the enantiomers of the rigid $D_1$ agonist, ODHX has been revealed for the first time.

Example 26

Materials and Methods for Examples 24 and 25. Chemicals and Reagents. [$^3$H] Cyclic AMP (30 Ci/mmol) was purchased from PerkinElmer (Boston, Mass., USA). Dopamine, clonidine, SCH-23390 and isobutyl-methylxanthine were purchased from Sigma-Aldrich Chemical Company (St. Louis, Mo., USA). Forskolin was purchased from Tocris Bioscience (San Diego, Calif., USA). Enantiomers of ODHX were synthesized as described previously (Cueva, J. P. et al. (2006) J. Med. Chem. 49:6848-6857).

Production of Cell Lines MCF7 and HEK $D_1$-CreLuc cells are described previously (Pitfield, S. E. et al. (2006) Oncology Res. 16:179-193; Cueva, J. P. et al. (2006) J. Med. Chem. 49:6848-6857). Briefly, HEK $D_1$-CreLuc cells were created by a two step process. HEK293 cells were co-transfected with the pBabe Puro and pGL-CreLuc vectors. Puromycin resistant clones, which expressed the functional cyclic AMP response element-linked luciferase reporter gene, were selected. Next, HEK-CreLuc cells were stably transfected with pcDNA3.1 (+)-$D_1$. Clones were assayed for $D_1$ receptor function by measuring cyclic AMP accumulation and luciferase activity. HEK-$\alpha_{2C}$ cells were constructed by stable transfection with pcDNA.3(+)-$\alpha_{2C}$. G418 resistant clones were selected and assayed for $\alpha_{2C}$ function by measuring inhibition of forskolin-stimulated cyclic AMP accumulation.

Cell Culture. HEK-$\alpha_{2C}$ cells were maintained in DMEM with 5% fetal clone serum, 5% bovine calf serum, 0.05 μg/ml penicillin, 50 μg/ml streptomycin, 25 μg/ml amphotericin B, and 300 μg/ml G418. MCF7 cells were maintained in MEM with 10% fetal clone III, 1.0 mM sodium pyruvate, 0.01 mg/ml insulin, 0.05 μg/ml penicillin, 50 μg/ml streptomycin, and 25 μg/ml amphotericin B. HEK-$D_1$ CRELuc were maintained in DMEM with 5% fetal clone serum, 5% bovine calf serum, 0.05 μg/ml penicillin, 50 μg/ml streptomycin, 25 μg/ml amphotericin B, 300 μg/ml G418, and 2 μg/ml puromycin. Cells were grown at 37° C. in a humidified incubator with 6% $CO_2$.

Cyclic AMP accumulation assay. Assays were performed on confluent monolayers of cells in 48-well plates. All drugs were diluted in Earle's balanced salt solution (EBSS) assay buffer (EBSS containing 2% bovine calf serum, 0.025% ascorbic acid, and 15 mM HEPES, pH 7.4) and added on ice. Cyclic AMP stimulation assays were performed on HEK $D_1$-CRELuc or MCF7 cells by incubating the cells with ligands for 15 minutes at 37° C. Cyclic AMP inhibition assays were performed on HEK-$\alpha_{2C}$ cells in the presence 30 μM forskolin to stimulate cyclic AMP formation. All assays were performed in the presence of 500 μM isobutylmethylxanthine (IBMX) and terminated with ice cold 3% trichloroacetic acid.

Cyclic AMP binding assay. Cyclic AMP accumulation assays were quantified in duplicate using a previously described protocol (Watts, V. J. et al. (1995) Synapse (New York, N.Y.) 21, 177-187). Briefly, cellular lysate (15-20 μL) was added to cyclic AMP binding buffer (100 mM Tris-HCl, pH 7.4, 100 mM NaCl, 5 mM EDTA) in assay tubes containing 1 nM final concentration [$^3$H]cyclic AMP and bovine adrenal gland cyclic AMP binding protein (100-150 μg in 500 μl binding buffer). The binding assay was incubated on ice at 4° C. for 2-4 hours and terminated by harvesting with ice cold wash buffer (10 mM Tris, 0.9% NaCl) using a 96-well Packard Filtermate cell harvester and Millipore Multiscreen Harvest Plates (Millipore, Billerica, Mass., USA). Packard Microscint O (40 μL) was added to each well after drying. Radioactivity was counted using a Packard Topcount scintillation counter. Standard curves ranging from 0.01 to 300 pmol of cyclic AMP were used to determine the concentration of cyclic AMP in each sample. Data analysis was performed on GraphPad Prism software.

Porcine Striatal Cyclase Assay. Fresh porcine brain tissue was provided by the Purdue Butcher Block. Striatal tissue was isolated by dissection and suspended in nine volumes of homogenization buffer (20 mM Hepes, 0.32 M sucrose, pH 7.4), followed by homogenization using 10-15 strokes with a Wheaton Teflon glass homogenizer. The homogenate was centrifuged at 1,000×g for 10 min at 4° C. The pellet was washed by resuspension in 10 ml of homogenization buffer and centrifuged again at 1000×g for 10 min at 4° C. The supernatants were combined and centrifuged at 30000×g for 10 min at 4° C. The pellet was resuspended in 20-100 ml of 50 mM Tris buffer (pH 7.4) by briefly using a Kinematica homogenizer, followed by centrifugation at 30,000×g for 30 min at 4° C. This pellet was resuspended again in 50 mM Tris buffer, dispensed into 1 ml aliquots, and centrifuged for 10 min at 13,000 g and 4° C. A BCA protein assay was used to determine the final protein concentration of the pellets. Supernatant was aspirated and the pellets were frozen at −80° C. until use.

The striatal cyclase assay was adapted from previously published methods (Bradley, K. D. et al. (2004) Synapse (New York, N.Y.) 53: 20-27). Assays were carried out in 96-well assay tubes containing reaction buffer (5 mM $MgCl_2$, 2 mM EDTA, 1 mM IBMX, 0.01% ascorbic acid, 10 μM pargyline, and 15 mM HEPES, pH 7.4), 20 μl reaction mix (1.25 mM adenosine 5'-triphosphate (ATP), 21.5 mM N-[Imino(phosphonoamino)methyl]-N-methylglycine disodium salt (phosphocreatine), and 3 U creatine phosphokinase), 1 μM Gpp(NH)p, 30 μg striatal protein, and the indicated drugs in a total volume of 100 μl. Duplicate samples for each treatment were incubated in a 30° C. water bath for 15 min. Adenylate cyclase activity was terminated by the addition of 200 μl of 3% trichloroacetic acid. The reaction tubes were covered with Parafilm and stored at 4° C. until the concentration of cyclic AMP was quantified as described above.

What is claimed is:
1. A compound of the formula:

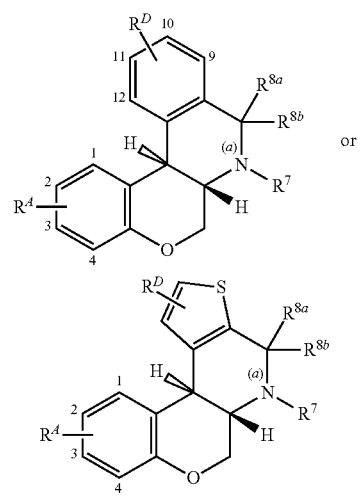

or a pharmaceutically acceptable salt thereof, wherein
$R^A$ represents from 1 to 4 substituents each independently selected from the group consisting of hydrogen, halo, optionally substituted alkyl, amino, acylamino, optionally substituted alkylsulfonyl, aminosulfonyl, nitro, and —$OR^{13}$, where $R^{13}$ is hydrogen, alkyl, acyl, alkanoyl, aryloyl, or a phenol protecting group, each of which is optionally substituted; or $R^A$ represents from 2 to 4 substituents, where 2 of said substituents are adjacent and are taken together to form an optionally substituted carbocyclic ring or a fused alkylenedioxy group, and each other substituent is independently selected from the group consisting of hydrogen, halo, optionally substituted alkyl, amino, acylamino, optionally substituted alkylsulfonyl, aminosulfonyl, nitro, and —$OR^{13}$, where $R^{13}$ is hydrogen, alkyl, acyl, alkanoyl, aryloyl, or a phenol protecting group, each of which is optionally substituted;

$R^D$ represents 1-4 substituents each independently selected from the group consisting of hydrogen, halo, optionally substituted alkyl, and optionally substituted alkoxy; or $R^D$ represents 2-4 substituents where 2 of said substituents are adjacent substituents and are taken together with the attached carbons to form an optionally substituted carbocycle or a fused alkylenedioxy group;

$R^7$ is selected from the group consisting of hydrogen and a group —$(CH_2)_{m'}Z'$, where m' is an integer from 0-6 and Z' is selected from the group consisting of hydrogen, halogen, hydroxy, formyl, $C_1$-$C_6$ alkanoyloxy, optionally substituted benzoyloxy, $C_1$-$C_6$ alkyl, $C_1$-$C_6$ alkoxy, $C_3$-$C_8$ cycloalkyl, $C_3$-$C_8$ cycloalkoxy, $C_2$-$C_6$ alkenyl, $C_2$-$C_6$ alkynyl, $C_1$-$C_6$ haloalkyl, $C_1$-$C_6$ haloalkoxy, $C_3$-$C_8$ halocycloalkyl, $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, nitro, $C_1$-$C_6$ alkylsulfonyl, optionally substituted phenyl, and optionally substituted phenoxy;

$R^{8a}$ is hydrogen; and $R^{8b}$ is hydrogen; or $R^{8a}$ and $R^{8b}$ are taken together to form a double-bonded oxygen; and (a) represents a single bond or a double bond; providing that when (a) is a double bond, the group $R^{8a}$ is absent.

2. The compound or salt of claim 1 wherein $R^A$ represents 2-$R^2$ and 3-$OR^{13}$; where $R^2$ is hydrogen, halo, optionally substituted alkyl, amino, acylamino, optionally substituted alkylsulfonyl, aminosulfonyl, or nitro; and $R^{13}$ is hydrogen, alkyl, acyl, or a phenol protecting group.

3. The compound or salt of claim 1 wherein $R^A$ represents 2-$OR^{13}$ and 3-$R^3$; where $R^{13}$ is hydrogen, alkyl, acyl, or a phenol protecting group; and $R^3$ is hydrogen, halo, optionally substituted alkyl, amino, acylamino, optionally substituted alkylsulfonyl, aminosulfonyl, or nitro.

4. The compound or salt of claim 1 wherein $R^A$ represents 2-$OR^{13}$ and 3-$OR^{13}$; where each $R^{13}$ is each independently selected from the group consisting of hydrogen, alkyl, acyl, or a phenol protecting group; or each $R^{13}$ is taken together with the other to form a methylene group.

5. The compound or salt of claim 1 wherein $R^A$ is 2,3-dihydroxy.

6. The compound or salt of claim 1 wherein $R^A$ is 2,3-($OR^{13}$)$_2$, where one $R^{13}$ is hydrogen or acetyl.

7. The compound or salt of claim 1 wherein $R^D$ represents from 1 to 4 substituents each independently selected from the group consisting of hydrogen, halo, alkyl, and alkoxy.

8. The compound or salt of claim 1 wherein $R^D$ is a substituent selected from the group consisting of hydrogen, halo, optionally substituted alkyl, and optionally substituted alkoxy.

9. The compound or salt of claim 1 wherein $R^7$ is hydrogen or optionally substituted alkyl.

10. The compound or salt of claim 1 wherein $R^{8a}$ and $R^{8b}$ are each hydrogen; and (a) is a single bond.

11. The compound or salt of claim 1 wherein $R^{8a}$ is absent; and (a) is a double bond.

12. The compound or salt of claim 1 wherein $R^{8a}$ and $R^{8b}$ are taken together to form a double-bonded oxygen; and (a) is a single bond.

13. The compound or salt of claim 1 wherein the compound has the formula:

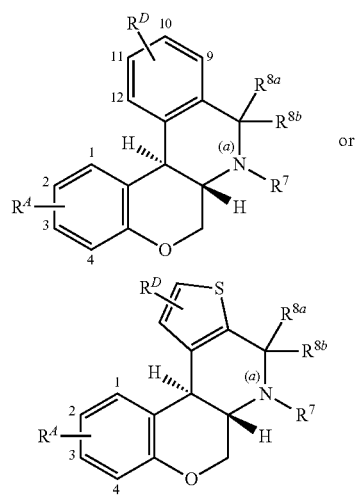

and is in substantially optically pure form.

14. The compound or salt of claim 1 wherein the compound has the formula:

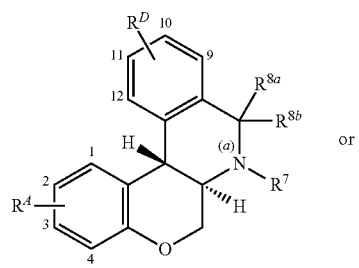

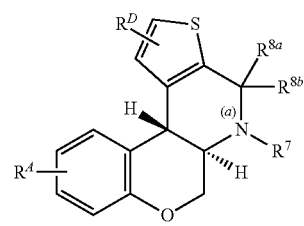

and is in substantially optically pure form.

15. A pharmaceutical composition comprising the compound or salt of claim 1, and a pharmaceutically acceptable carrier, diluent, excipient, or a combination thereof.

16. A process for preparing the compound or salt of claim 1 of the formula

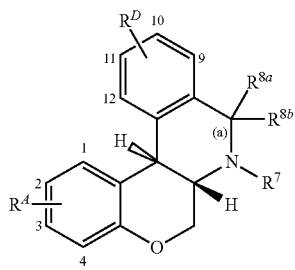

wherein $R^{8a}$ and $R^{8b}$ are each hydrogen; and (a) is a single bond, or wherein $R^{8a}$ is absent; and (a) is a double bond, the process comprising the step of reacting a compound of the formula:

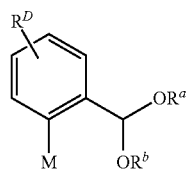

with a compound of the formula

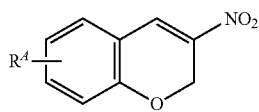

to prepare a compound of the formula

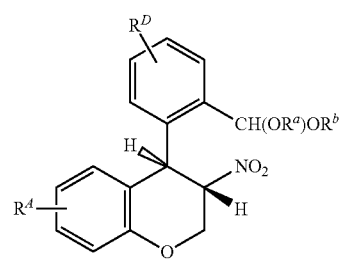

where M is a metal or metal salt; $R^a$ and $R^b$ are each an independently selected oxygen protecting group, or $R^a$ and $R^b$ are taken together to form a cyclic geminal oxygen protecting group; and $R^A$ and $R^D$ are as defined in claim 1.

17. A compound of the formula

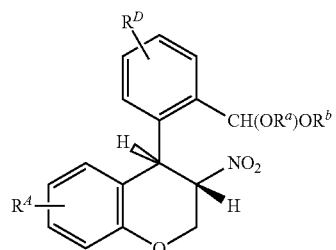

where $R^a$ and $R^b$ are each an independently selected oxygen protecting group, or $R^a$ and $R^b$ are taken together to form a cyclic geminal oxygen protecting group; and $R^A$ and $R^D$ are as defined in claim 1.

18. The process of claim 16 wherein $R^a$ and $R^b$ are taken together to form an alkylene.

19. The compound of claim 17 wherein $R^a$ and $R^b$ are taken together to form an alkylene.

20. The process of claim 16 wherein M is selected from the group consisting of lithium, a magnesium, and a zinc salt.

21. The process of claim 16 further comprising the step of reducing a compound of the formula

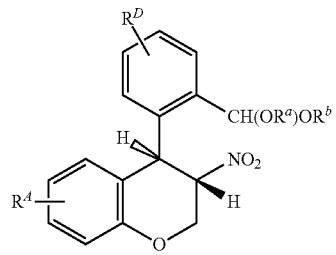

to prepare a compound of the formula

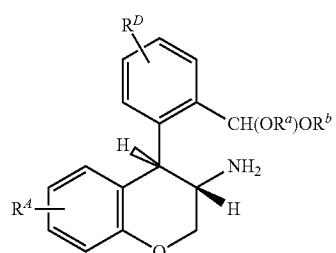

where $R^a$ and $R^b$ are each an independently selected oxygen protecting group, or $R^a$ and $R^b$ are taken together to form a cyclic geminal oxygen protecting group; and $R^A$ and $R^D$ are as defined in claim 1.

22. A compound of the formula

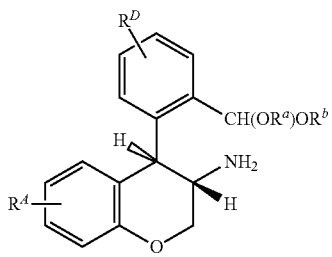

where $R^a$ and $R^b$ are each an independently selected oxygen protecting group, or $R^a$ and $R^b$ are taken together to form a cyclic geminal oxygen protecting group; and $R^A$ and $R^D$ are as defined in claim 1.

23. A process for preparing the compound or salt of claim 1 of the formula

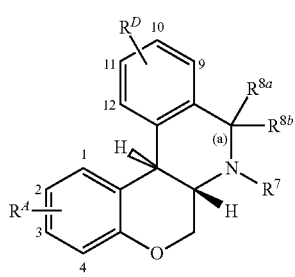

wherein $R^{8a}$ and $R^{8b}$ are each hydrogen; and (a) is a single bond, or wherein $R^{8a}$ and $R^{8b}$ are taken together to form a double-bonded oxygen; and (a) is a single bond, the process comprising the step of reacting a compound of the formula:

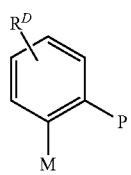

with a compound of the formula

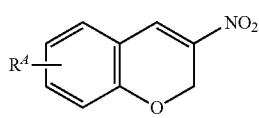

to prepare a compound of the formula

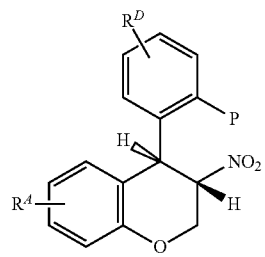

where M is a metal or metal salt; P is an oxazoline protected carboxylic acid derivative; and $R^A$ and $R^D$ are as defined in claim 1.

24. A compound of the formula

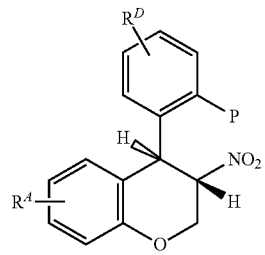

where P is an oxazoline protected carboxylic acid derivative; and $R^A$ and $R^D$ are as defined in claim 1.

25. A compound of the formula:

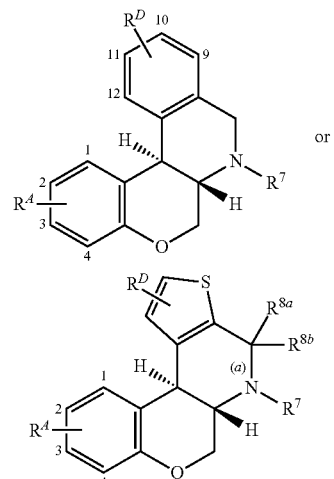

or a pharmaceutically acceptable salt thereof, in substantially optically pure form; wherein $R^A$ represents from 1 to 4 substituents each independently selected from the group consisting of hydrogen, halo, optionally substituted alkyl, amino, acylamino, optionally substituted alkylsulfonyl, aminosulfonyl, nitro, and —$OR^{13}$, where $R^{13}$ is hydrogen, alkyl, acyl, alkanoyl, aryloyl, or a phenol protecting group, each of which is optionally substituted; or $R^A$ represents from 2 to 4 substituents, where 2 of said substituents are adjacent and are taken together to form an optionally substituted carbocyclic ring or a fused alkylenedioxy group, and each other substituent is independently selected from the group consisting of hydrogen, halo, optionally substituted alkyl, amino, acylamino, optionally substituted alkylsulfonyl, aminosulfonyl, nitro, and —OR$^{13}$, where R$^{13}$ is hydrogen, alkyl, acyl, alkanoyl, aryloyl, or a phenol protecting group, each of which is optionally substituted;

R$^D$ represents 1-4 substituents each independently selected from the group consisting of hydrogen, halo, optionally substituted alkyl, and optionally substituted alkoxy; or R$^D$ represents 2-4 substituents where 2 of said substituents are adjacent substituents and are taken together with the attached carbons to form an optionally substituted carbocycle or a fused alkylenedioxy group;

R$^7$ is selected from the group consisting of hydrogen and a group —(CH$_2$)$_{m'}$Z', where m' is an integer from 0-6 and Z' is selected from the group consisting of hydrogen, halogen, hydroxy, formyl, C$_1$-C$_6$ alkanoyloxy, optionally substituted benzoyloxy, C$_1$-C$_6$ alkyl, C$_1$-C$_6$ alkoxy, C$_3$-C$_8$ cycloalkyl, C$_3$-C$_8$ cycloalkoxy, C$_2$-C$_6$ alkenyl, C$_2$-C$_6$ alkynyl, C$_1$-C$_6$ haloalkyl, C$_1$-C$_6$ haloalkoxy, C$_3$-C$_8$ halocycloalkyl, C$_3$-C$_8$ halocycloalkoxy, amino, C$_1$-C$_6$ alkylamino, (C$_1$-C$_6$ alkyl)(C$_1$-C$_6$ alkyl)amino, alkylcarbonylamino, N—(C$_1$-C$_6$ alkyl)alkylcarbonylamino, aminoalkyl, C$_1$-C$_6$ alkylaminoalkyl, (C$_1$-C$_6$ alkyl)(C$_1$-C$_6$ alkyl)aminoalkyl, alkylcarbonylaminoalkyl, N—(C$_1$-C$_6$ alkyl)alkylcarbonylaminoalkyl, cyano, nitro, C$_1$-C$_6$ alkylsulfonyl, optionally substituted phenyl, and optionally substituted phenoxy;

R$^{8a}$ is hydrogen; and R$^{8b}$ is hydrogen; or R$^{8a}$ and R$^{8b}$ are taken together to form a double-bonded oxygen; and (a) represents a single bond or a double bond; providing that when (a) is a double bond, the group R$^{8a}$ is absent.

26. The compound or salt of claim 25 wherein R$^A$ represents 2-R$^2$ and 3-OR$^{13}$; where R$^2$ is hydrogen, halo, optionally substituted alkyl, amino, acylamino, optionally substituted alkylsulfonyl, aminosulfonyl, or nitro; and R$^{13}$ is hydrogen, alkyl, acyl, or a phenol protecting group.

27. The compound or salt of claim 25 wherein R$^A$ represents 2-OR$^{13}$ and 3-R$^3$; where R$^{13}$ is hydrogen, alkyl, acyl, or a phenol protecting group; and R$^3$ is hydrogen, halo, optionally substituted alkyl, amino, acylamino, optionally substituted alkylsulfonyl, aminosulfonyl, or nitro.

28. The compound or salt of claim 25 wherein R$^A$ represents 2-OR$^{13}$ and 3-OR$^{13}$; where each R$^{13}$ is each independently selected from the group consisting of hydrogen, alkyl, acyl, or a phenol protecting group; or each R$^{13}$ is taken together with the other to form a methylene group.

29. The compound or salt of claim 25 wherein R$^A$ is 2,3-dihydroxy.

30. The compound or salt of claim 25 wherein R$^A$ is 2,3-(OR$^{13}$)$_2$, where one R$^{13}$ is hydrogen or acetyl.

31. The compound or salt of claim 25 wherein R$^D$ represents from 1 to 4 substituents each independently selected from the group consisting of hydrogen, halo, alkyl, and alkoxy.

32. The compound or salt of claim 25 wherein R$^D$ is a substituent selected from the group consisting of hydrogen, halo, optionally substituted alkyl, and optionally substituted alkoxy.

33. The compound or salt of claim 25 wherein R$^7$ is hydrogen or optionally substituted alkyl.

34. A pharmaceutical composition comprising the compound or salt of claim 25, and a pharmaceutically acceptable carrier, diluent, excipient, or a combination thereof.

35. A method for treating dopamine-related disorders or dysfunctions in a patient by administering to the patient a therapeutically effective amount of a compound of the formula:

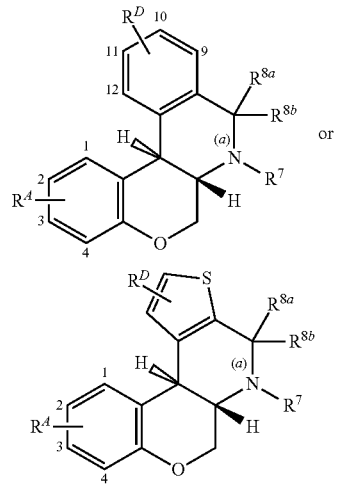

wherein
R$^A$ represents from 1 to 4 substituents each independently selected from the group consisting of hydrogen, halo, optionally substituted alkyl, amino, acylamino, optionally substituted alkylsulfonyl, aminosulfonyl, nitro, and —OR$^{13}$, where R$^{13}$ is hydrogen, alkyl, acyl, alkanoyl, aryloyl, or a phenol protecting group, each of which is optionally substituted; or R$^A$ represents from 2 to 4 substituents, where 2 of said substituents are adjacent and are taken together to form an optionally substituted carbocyclic ring or a fused alkylenedioxy group, and each other substituent is independently selected from the group consisting of hydrogen, halo, optionally substituted alkyl, amino, acylamino, optionally substituted alkylsulfonyl, aminosulfonyl, nitro, and —OR$^{13}$, where R$^{13}$ is hydrogen, alkyl, acyl, alkanoyl, aryloyl, or a phenol protecting group, each of which is optionally substituted;

R$^D$ represents 1-4 substituents each independently selected from the group consisting of hydrogen, halo, optionally substituted alkyl, and optionally substituted alkoxy; or R$^D$ represents 2-4 substituents where 2 of said substituents are adjacent substituents and are taken together with the attached carbons to form an optionally substituted carbocycle or a fused alkylenedioxy group;

R$^7$ is selected from the group consisting of hydrogen and a group —(CH$_2$)$_{m'}$Z', where m' is an integer from 0-6 and Z' is selected from the group consisting of hydrogen, halogen, hydroxy, formyl, C$_1$-C$_6$ alkanoyloxy, optionally substituted benzoyloxy, C$_1$-C$_6$ alkyl, C$_1$-C$_6$ alkoxy, C$_3$-C$_8$ cycloalkyl, C$_3$-C$_8$ cycloalkoxy, C$_2$-C$_6$ alkenyl, C$_2$-C$_6$ alkynyl, C$_1$-C$_6$ haloalkyl, C$_1$-C$_6$ haloalkoxy, C$_3$-C$_8$ halocycloalkyl, C$_3$-C$_8$ halocycloalkoxy, amino, C$_1$-C$_6$ alkylamino, (C$_1$-C$_6$ alkyl)(C$_1$-C$_6$ alkyl)amino, alkylcarbonylamino, N—(C$_1$-C$_6$ alkyl)alkylcarbonylamino, aminoalkyl, C$_1$-C$_6$ alkylaminoalkyl, (C₁-C₆ alkyl)(C₁-C₆ alkyl)aminoalkyl, alkylcarbonylaminoalkyl, N—(C₁-C₆ alkyl)alkylcarbonylaminoalkyl, cyano, nitro, C₁-C₆ alkylsulfonyl, optionally substituted phenyl, and optionally substituted phenoxy;

$R^{8a}$ is hydrogen; and $R^{8b}$ is hydrogen; or $R^{8a}$ and $R^{8b}$ are taken together to form a double-bonded oxygen; and (a) represents a single bond or a double bond; providing that when (a) is a double bond, the group $R^{8a}$ is absent; or pharmaceutically acceptable salts thereof.

36. The compound or salt of claim 1 which is a compound of the formula:

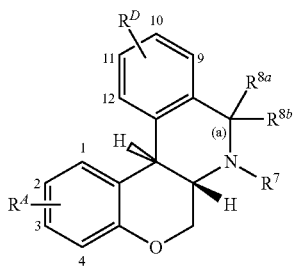

or a pharmaceutically acceptable salt thereof, wherein
$R^4$ represents from 1 to 4 substituents each independently selected from the group consisting of hydrogen, halo, optionally substituted alkyl, amino, acylamino, optionally substituted alkylsulfonyl, aminosulfonyl, nitro, and —OR¹³, where R¹³ is hydrogen, alkyl, acyl, alkanoyl, aryloyl, or a phenol protecting group, each of which is optionally substituted; or $R^4$ represents from 2 to 4 substituents, where 2 of said substituents are adjacent and are taken together to form an optionally substituted carbocyclic ring or a fused alkylenedioxy group, and each other substituent is independently selected from the group consisting of hydrogen, halo, optionally substituted alkyl, amino, acylamino, optionally substituted alkylsulfonyl, aminosulfonyl, nitro, and —OR¹³, where R¹³ is hydrogen, alkyl, acyl, alkanoyl, aryloyl, or a phenol protecting group, each of which is optionally substituted;

$R^D$ represents 1-4 substituents each independently selected from the group consisting of hydrogen, halo, optionally substituted alkyl, and optionally substituted alkoxy; or $R^D$ represents 2-4 substituents where 2 of said substituents are adjacent substituents and are taken together with the attached carbons to form an optionally substituted carbocycle or a fused alkylenedioxy group;

$R^7$ is selected from the group consisting of hydrogen and a group —(CH₂)ₘ'Z', where m' is an integer from 0-6 and Z' is selected from the group consisting of hydrogen, halogen, hydroxy, formyl, C₁-C₆ alkanoyloxy, optionally substituted benzoyloxy, C₁-C₆ alkyl, C₁-C₆ alkoxy, C₃-C₈ cycloalkyl, C₃-C₈ cycloalkoxy, C₂-C₆ alkenyl, C₂-C₆ alkynyl, C₁-C₆ haloalkyl, C₁-C₆ haloalkoxy, C₃-C₈ halocycloalkyl, C₃-C₈ halocycloalkoxy, amino, C₁-C₆ alkylamino, (C₁-C₆ alkyl)(C₁-C₆ alkyl)amino, alkylcarbonylamino, N—(C₁-C₆ alkyl)alkylcarbonylamino, aminoalkyl, C₁-C₆ alkylaminoalkyl, (C₁-C₆ alkyl)(C₁-C₆ alkyl)aminoalkyl, alkylcarbonylaminoalkyl, N—(C₁-C₆ alkyl)alkylcarbonylaminoalkyl, cyano, nitro, C₁-C₆ alkylsulfonyl, optionally substituted phenyl, and optionally substituted phenoxy;

$R^{8a}$ is hydrogen; and $R^{8b}$ is hydrogen; or $R^{8a}$ and $R^{8b}$ are taken together to form a double-bonded oxygen; and (a) represents a single bond or a double bond; providing that when (a) is a double bond, the group $R^{8a}$ is absent.

37. The compound or salt of claim 36 wherein $R^A$ represents 2-R² and 3-OR¹³; where R² is hydrogen, halo, optionally substituted alkyl, amino, acylamino, optionally substituted alkylsulfonyl, aminosulfonyl, or nitro; and R¹³ is hydrogen, alkyl, acyl, or a phenol protecting group.

38. The compound of claim 36 wherein $R^A$ represents 2-OR¹³ and 3-R³; where R¹³ is hydrogen, alkyl, acyl, or a phenol protecting group; and R³ is hydrogen, halo, optionally substituted alkyl, amino, acylamino, optionally substituted alkylsulfonyl, aminosulfonyl, or nitro.

39. The compound of claim 36 wherein $R^A$ represents 2-OR¹³ and 3-OR¹³; where each R¹³ is each independently selected from the group consisting of hydrogen, alkyl, acyl, or a phenol protecting group; or each R¹³ is taken together with the other to form a methylene group.

40. The compound or salt of claim 36 wherein R⁷ is hydrogen or optionally substituted alkyl.

41. The compound of claim 36 wherein $R^{8a}$ and $R^{8b}$ are each hydrogen; and (a) is a single bond.

42. The compound of claim 36 wherein the compound has the formula:

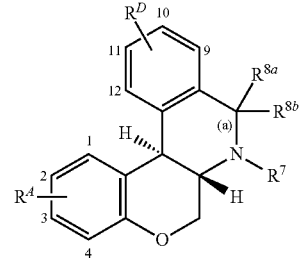

and is in substantially optically pure form.

43. A pharmaceutical composition comprising the compound of claim 36, and a pharmaceutically acceptable carrier, diluent, excipient, or a combination thereof.

44. The compound of claim 10 wherein the compound has the formula:

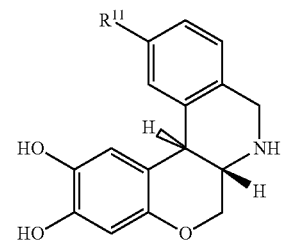

wherein R¹¹ is hydrogen, methyl, ethyl or fluoro, or a pharmaceutically acceptable salt thereof.

45. The compound of claim 42 which is (+)-(6aS,12bR)-2,3-dihydroxy-6a,7,8,12b-tetrahydro-6H-chromeno[3,4-c]isoquinoline, or a pharmaceutically acceptable salt thereof.

* * * * *